(12) United States Patent
Dixon et al.

(10) Patent No.: US 7,888,553 B2
(45) Date of Patent: Feb. 15, 2011

(54) METHOD FOR MODIFYING LIGNIN COMPOSITION AND INCREASING IN VIVO DIGESTIBILITY OF FORAGES

(75) Inventors: Richard A. Dixon, Ardmore, OK (US); Dianjing Guo, Hong Kong (CN)

(73) Assignee: The Samuel Roberts Noble Foundation, Ardmore, OK (US)

( * ) Notice: Subject to any disclaimer, the term of this patent is extended or adjusted under 35 U.S.C. 154(b) by 125 days.

(21) Appl. No.: 12/152,671

(22) Filed: May 14, 2008

(65) Prior Publication Data
US 2009/0044294 A1 Feb. 12, 2009

Related U.S. Application Data

(62) Division of application No. 10/239,463, filed as application No. PCT/US01/09398 on Mar. 23, 2001, now abandoned.

(60) Provisional application No. 60/192,086, filed on Mar. 24, 2000.

(51) Int. Cl.
*C12N 15/82* (2006.01)
*A01H 5/00* (2006.01)
(52) U.S. Cl. .................. 800/278; 800/287; 800/286; 800/285; 800/298
(58) Field of Classification Search .................. None
See application file for complete search history.

(56) References Cited

U.S. PATENT DOCUMENTS

| 5,451,514 A | 9/1995 | Boudet et al. ............. 435/172.3 |
| 5,850,020 A | 12/1998 | Bloksberg et al. ........... 800/205 |
| 5,922,928 A | 7/1999 | Chiang et al. .............. 800/278 |

FOREIGN PATENT DOCUMENTS

| WO | WO 93/05160 | 3/1993 |
| WO | WO 94/23044 | * 10/1994 |
| WO | WO 98/03535 | * 1/1998 |

OTHER PUBLICATIONS

Baucher et al (1999, Plant Molecular Biology 39:437-447).*
Zhong et al (1998, The Plant Cell 10:2033-2045).*
Liang et al (1989, PNAS 86:9284-9288).*
Albrecht et al., "Cell-wall composition and digestibility of alfalfa stems and leaves," *Crop Sci.*, 27:735-741, 1987.
Atanassova et al., "Altered lignin composition in transgenic tobacco expressing O-methyltransferase sequences in sense and antisense orientation," *Plant J.*, 8:465-477, 1995.
Baucher et al., "Down-regulation of cinnamyl alcohol dehydrogenase in transgenic alfalfa (*Medicago sativa* L.) and the effect on lignin composition and digestibility," *Plant Mol. Biol.*, 39:437-447, 1999.
Boudet et al., "Lignin genetic engineering," *Molecular Breeding*, 2:25-39, 1996.

Boudet et al., "Tansley review No. 80: Biochemistry and molecular biology of lignification," *New Phytologist*, 129:203-236, 1995.
Bowie et al., "Deciphering the message in protein sequences: tolerance to amino acid substitution," *Science*, 247:1306-1310, 1990.
Buxton et al., "Lignin constituents and cell wall digestibility of grass and legume stems," *Crop Sci.*, 28:553-558, 1988.
Casler, "In vitro digestibility of dry matter and cell wall constituents of smooth bromegrass forage," *Crop Sci.*, 27:931-934, 1987.
Chen et al., "Evidence for a novel biosynthetic pathway that regulates the ratio of syringyl to guaiacyl residues in lignin in the differentiating xylem of *Magnolia kobus* DC," *Planta*, 207:597-603, 1999.
Church et al., "Genomic sequencing," *Proc. Natl. Acad. Sci. USA*, 81:1991-1995, 1984.
Colliver et al, "Differential modification of flavonoid and isoflavonoid biosynthesis with an antisense chalcone synthase construct in transgenic *Lotus corniculatus*," *Plant Mol. Biol.*, 35:509-522, 1997.
Cox et al., "Analysis of plant gene expression," In: Plant Molecular Biology. A Practical Approach, C.H. Shaw, Ed., Oxford, IRL Press, pp. 1-35, 1988.
Cramer et al., "Phenylalanine ammonia-lyase gene organization and structure," *Plant Mol. Biol.*, 12:367-383, 1989.
Davin et al., "Phenylpropanoid metabolism: biosynthesis of monolignols, lignans and neolignans, lignins and suberins," *Rec. Adv. Phytochem.*, 26:325-375, 1992.
Dixon et al., "Genetic manipulation of lignin and phenylpropanoid compounds involved in interactions with microorganisms," *Rec. Adv. Phytochem.*, 28:153-178, 1994.
Emery et al., "Radial patterning of arabidopsis shoots by class III HD-ZIP and Kanadi genes," *Current Biology*, 13:1768-1774, 2003.
Franke et al., "Modified lignin in tobacco and poplar plants overexpressing the arabidopsis gene encoding ferulate 5-hybdroxylase," *The Plant J.*, 22(3)::223-234, 2000.
Garbarino et al., "Isolation of a ubiquitin-ribosomal protein gene (ubi3) from potato and expression of its promoter in transgenic plants," *Plant Mol. Biol.*, 24:119-127, 1994.
Gowri et al, "Stress responses in alfalfa (*Medicago sativa* L.) X. Molecular cloning and expression of S-adenosyl-L-methionine: caffeic acid 3-O-methyltransferase, a key enzyme of lignin biosynthesis," *Plant Physiol.*, 97:7-14, 1991.
Grabber et al., "Digestion kinetics of parenchyma and sclerenchyma cell walls isolated from orchardgrass and switchgrass," *Crop Sci.*, 32:806-810, 1992.
Grabber et al., "p-Coumaroylated syringyl units in maize lignin: implications for β-ether cleavage by thioacidolysis," *Phytochemistry*, 43:1189-1194, 1996.

(Continued)

*Primary Examiner*—Stuart F. Baum
(74) *Attorney, Agent, or Firm*—SNR Denton US LLP

(57) ABSTRACT

Methods for transforming forage legumes or woody plants with a DNA construct comprising at least one open reading frame encoding for a caffeoyl CoA 3-O-methyltransferase enzyme and a caffeic acid 3-O-methyltransferase enzyme or fragment thereof in either a sense or antisense orientation under a lignification-associated tissue specific promoter have been found, resulting in the down-regulation of the corresponding homologous gene either through antisense inhibition or sense suppression, as well as reduced lignin content and modified lignin composition in the transgenic plants. The expression of the caffeoyl CoA 3-O-methyltransferase transgene produces an increased syringyl lignin to guaiacyl lignin ratio in the transformed plant, and greatly improved forage digestibility.

11 Claims, 8 Drawing Sheets

OTHER PUBLICATIONS

Grabber et al., "p-hydroxyphenyl, guaiacyl, and syringyl lignins have similar inhibitory effects on wall degradability," *J. Agric. Food Chem.*, 45:2530-2532, 1997.

Guo et al., "Downregulation of cafeic acid 3-O-methyltransferase and caffeoyl 3-O-methyltransferase in transgenic alfalfa: impacts on lignin structure and implications for the biosynthesis of G and S lignin," *Plant Cell*, 13:73-88, 2001.

Halpin et al., "Manipulation of lignin quality by down-regulation of cinnamyl alcohol dehydrogenase," *Plant J.*, 6:339-350, 1994.

Humphreys et al., "New routes for lignin biosynthesis defined by biochemical characterization of recombinant ferulate 5-hydroxylase, a multifunctional cytochrome P450-dependent monooxygenase," *Proc. Natl. Acad Sci.*, 96:10045-10050, 1999.

Inoue et al., "Developmental expression and substrate specificities of alfalfa caffeic acid 3-O-methyltranferase and caffeoyl CoA 3-O-methyltransferase in relation to lignification," *Plant Physiol.*, 117:761-770, 1998.

Inoue et al., "Substrate preferences of caffeic acid/5-hydroxyferulic acid 3-O-methyltransferases in developing stems of alfalfa (*Medicago sativa* L.)," *Arch Biochem Biophys.*, 375:175-182, 2000.

Irdani et aL, "Construction of a new vector conferring methotrexate resistance in *Nicotiana tabacum* plants," *Plant Mol. Biol.*, 37:1079-1084, 1998.

Jung et al., "Influence of lignin on digestibility of forage cell wall material," *J. Anim. Sci.*, 62:1703-1712, 1986.

Kersey et al., "Immunolocalization of two lignin O-methyltransferases in stems of alfalfa (*Medicago sativa* L.," *Protoplasma*, 209:46-57, 1999.

Lapierre et al., "Thioacidolysis of lignin: Comparison with acidolysis," *J. Wood Chem. Technol.*, 5:277-283, 286-292, 1985.

Lewis et al., "Lignin: occurrence, biogenesis and biodegradation," *Annu. Rev. Plant Physiol. Plant Mol. Biol.*, 41:455-496, 1990.

Lewis, "A 20$^{th}$ century roller coaster ride: a short account of lignification," *Current Opinion in Plant Biology*, 2:153-162, 1999.

Leyva et al., "Cis-element combinations determine phenylalanine ammonia-lyase gene tissue specific expression patterns," *Plant Cell*, 4:263-271, 1992.

Li et al., "5-hydroxyconiferyl aldehyde modulates enzymatic methylation for syringyl monolignol formation, a new view of monolignol biosynthesis in angiosperms," *J. Biol. Chem.*, 275:6537-6545, 2000.

Liang et al., "Developmental and environmental regulation of a phenylalanine ammonia-lyase 13-glucuronidase gene fusion in transgenic tobacco plants," *Proc. Natl. Acad. Sci. USA*, 86:9284-9288, 1989.

McConnell et al., "Role of phabulosa and phavoluta in determining radial patterning in shoots," *Nature*, 411(6838):709-713, 2001.

Meyer et al., "Lignin monomer composition is determined by the expression of a cytochrome P450-dependent monoxygenase in arabidopsis," *Proc. Natl. Acad. Sci. USA*, 95:6619-6623, 1998.

Ni et al., "Reduced lignin in transgenic plants containing an engineered caffeic acid O-methyltransferase antisense gene," *Transgenic Res.*, 3:120-126, 1994.

Osakabe et al., "Coniferyl aldehyde 5-hydroxylation and methylation direct syringyl lignin biosynthesis in angiosperms," *Proc. Natl. Acad. Sci. USA*, 96:8955-8960, 1999.

Pakusch et al., "S-adenosyl-L-methionine: trans-caffeoyl-coenzyme A 3-O-methyltransferase from elicitor-treated parsley cell suspension cultures," *Arch. Biochem Biophys.*, 271:488-494, 1989.

Piquemal et al., "Down-regulation of cinnamoyl-CoA reductase induces significant changes of lignin profiles in transgenic tobacco plants," *Plant J.*, 13:71-83, 1998.

Reimann-Philipp et al., "Coat protein-mediated resistance in transgenic tobacco expressing the tobacco mosaic virus coat protein from tissue-specific promoters," *Mol. Plant Microbe Interact*, 6:323-330, 1993.

Sederoff et al., "Unexpected variation in lignin," *Current Opinion in Plant Biology*, 2:145-152, 1999.

Sewalt et al., "Lignin impact on fiber degradation. 1. Quinone methide intermediates formed from lignin during in vitro fermentation of corn stover," *J. Sci. Food Agric.*, 71:195-203, 1996.

Shahin et al., "Transformation of cultivated alfalfa using disarmed *Agrobacterium tumefaciens*," *Crop Sci.*, 26:1235-1239, 1986.

Shufflebottom et al., "Transcription of two members of a gene family encoding phenylalanine ammonia-lyase leads to remarkably different cell specificities and induction patterns," *Plant J.*, 3:835-845, 1993.

Tabe et al., "Genetic engineering of grain and pasture legumes for improved nutritive value," *Genetica*, 90:181-200, 1993.

Thomas et al., "Selection of interspecific somatic hybrids of Medicago by using Agrobacterium-transformed tissues," *Plant Sci.*, 69:189-198, 1990.

Van Doorsselaere et al., "A novel lignin in popular trees with a reduced caffeic acid/5-hydroxyferulic acid O-methyltransferase activity," *Plant J.*, 8:855-864, 1995.

Vaucheret et al., "Transgene-induced gene silencing in plants," *Plant J.*, 16:651-659, 1998.

Whetten et al., "Genetic engineering of wood," *Forest Ecology and Management*, 43:301-316, 1991.

Ye et al., "An alternative methylation pathway in lignin biosynthesis in *Zinnia*," *Plant Cell*, 6:1427-1439, 1994.

Zhong et al., "Duel methylation pathways in lignin biosynthesis," *Plant Cell*, 10:2033-2045, 1998.

* cited by examiner

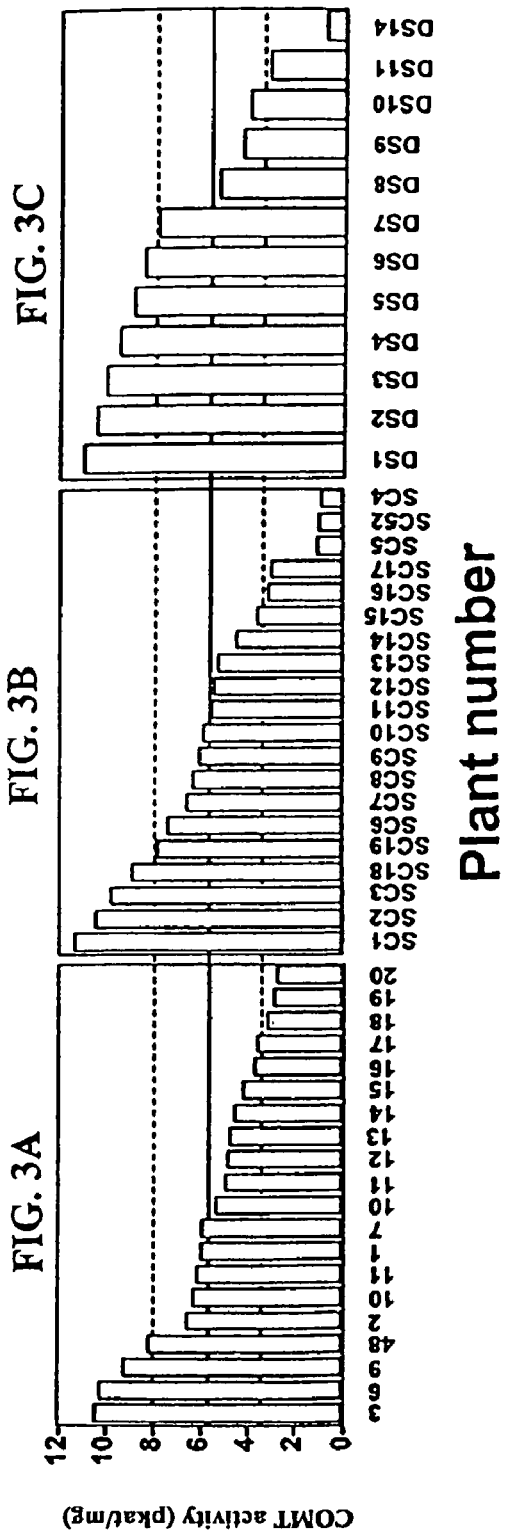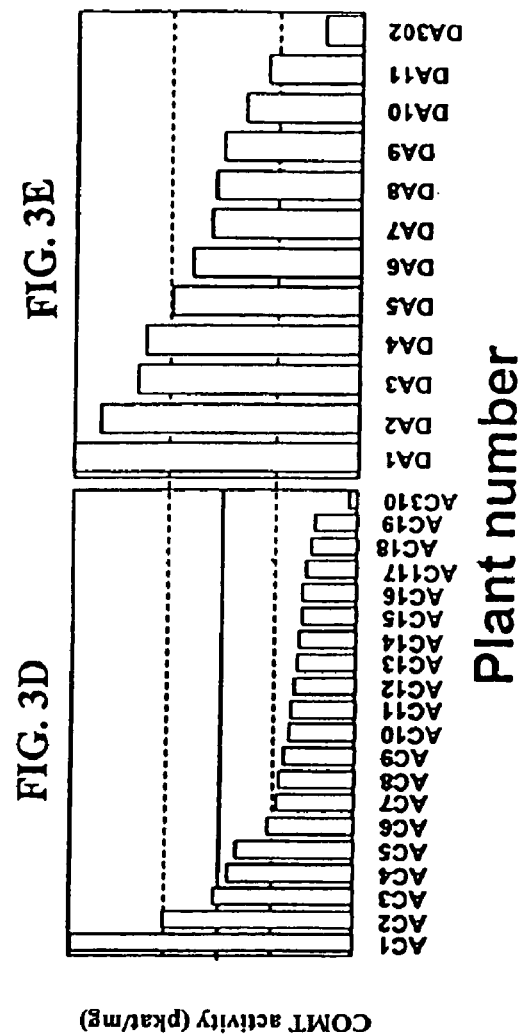

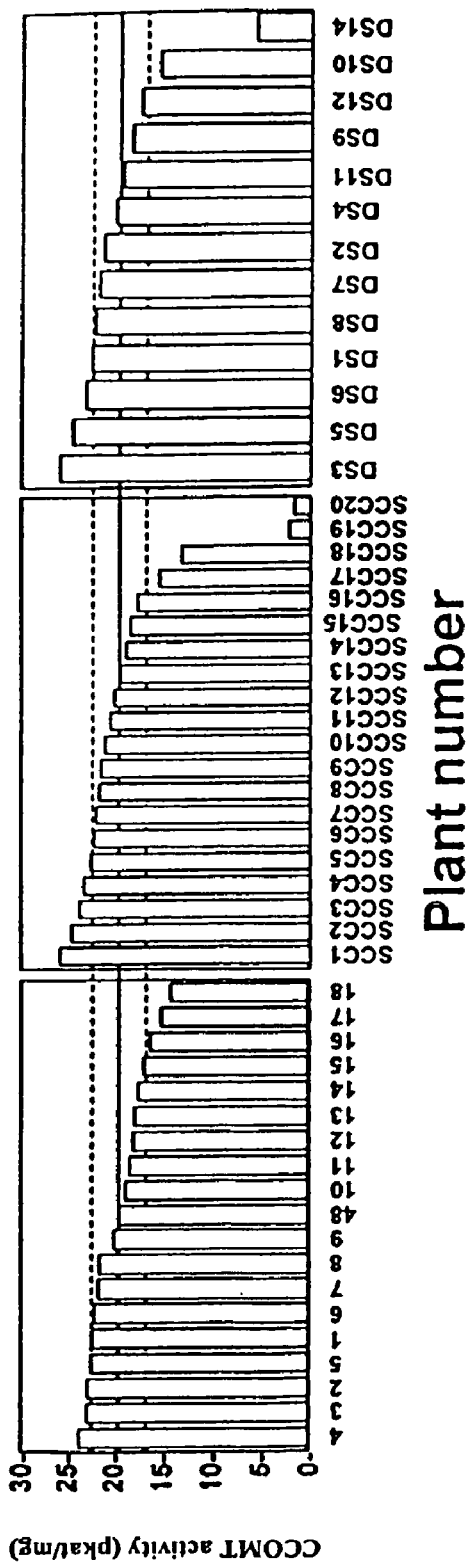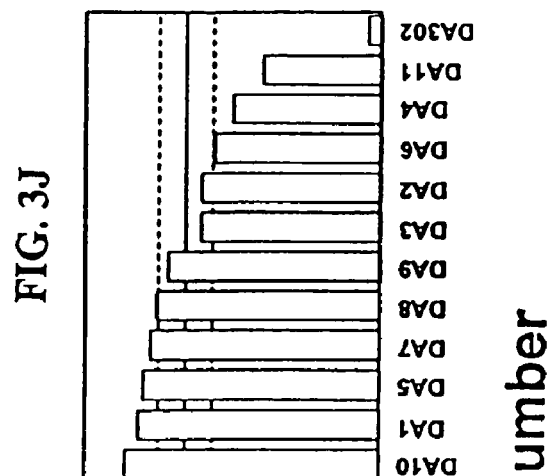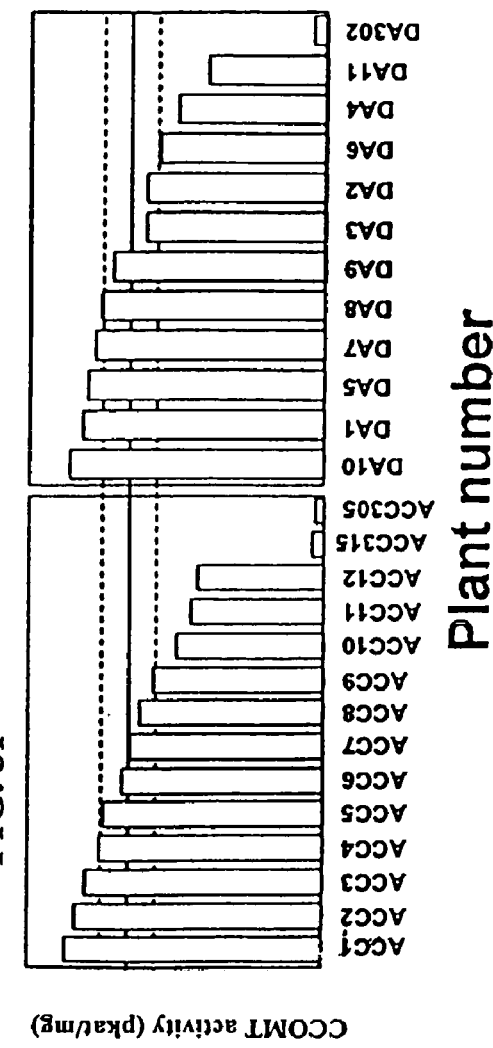

```
  31 atgggttcaa caggtgaaac tcaaataaca
  61 ccaacccaca tatcagatga agaagcaaac ctcttcgcca agtgcttca
 121 gttcttccca tgattttgaa atcagctctt gaacttgatc tgcaactagc cattgctaaa
 181 gctggacctg gtgctcaaat ttcacctatt gaaattgctt ctcagctacc aacaactaac
 241 cctgatgcac cagttatgtt ggaccgaatg ttgcgtctct tggcttgtta cataatcctc
 301 acatgttcag ttcgtactca acaagatgaa aaggttcaga gactttatgg tttggctact
 361 gttgctaagt atttggttaa gaatgaagat ggtgtatcca tttctgctct taatctcatg
 421 aatcaggata aagtgctcat ggaaagctgg taccacctaa aagatgcagt cctgatggg
 481 ggcattccat tcaacaaggc ttatggaatg acagcctttg aataccatgg aacagatcca
 541 aggttttaaca aggttttcaa caagggggat tctgatcact ctaccatcac aatgaagaaa
 601 attctttgaga cctacacagg ttttgaaggc cttaaatctc ttgttgatgt agtggttggt
 661 actggagctg taattaacac gattgtctca aaatatccca ctataaaggg tataaatttt
 721 gatttacccc atgtcattga agatgctcca tcttatccag gagttgagca tgttggtgga
 781 gacatgtttg tcagtattcc aaaggctgat gctgttttta tgaagtggat ttgtcatgac
 841 tggagtgatg agcactgctt gaaatttttg aagaactgct atgaggcact gccagacaat
 901 ggaaaagtga ttgtggcaga atgcatactt ccagtggctc cagattcaag cctggccaca
 961 aaaggtgtgg ttcacattga tgtgatcatg ttggctcata tcctggtgg gaaagagaga
1021 acacaaaaag agtttgagga tcttgccaaa ggtgctggat tccaaggttt caaagtccat
1081 tgtaatgctt tcaacacata catcatggag tttcttaaga aggttttaa
```

FIG. 5

```
 36 atggc aaccaacgaa gatcaaaagc
 61 aaactgaatc tggaagacat caagaagttg gtcacaagag tctttacaa agtgatgctc
121 tttaccagta tattctagag accagtgtct tcccaagaga acatgaagcc atgaaagagt
181 tgagagaggt cacagcaaaa cacccatgga acatcatgac aacctctgca gatgaaggac
241 aatttttgag catgctcctt aaacttatca atgctaagaa taccatggaa attggtgtct
301 acactggcta ctcccctcct gccactgccc tagctattcc tgaagatgga aagattttgg
361 ctatggacat taacaaagaa aattacgaat tgggtctacc tgtaattaaa aaagctggtg
421 ttgatcacaa aattgatttc agagaaggtc cagctcttcc agttcttgat gaaatgatca
481 aagacgaaaa gaatcatggt agctacgatt tcattttgt ggatgctgac aaaagacaatt
541 acctcaacta ttaattgatc ttgttaaagt gggaggtgtg atcgggtacg
601 acaaacactt ccataagagg atggaatgga tctgtggttg cacccctga tgctccattg aggaagtatg
661 ttaggtacta tagagatttt gttttggagc ttaacaaggc tttggctgtg gacctagga
721 ttgaaatatg tatgcttcct gttggtgatg gaatcactat ctgccgtagg atcaagtaa
```

METHOD FOR MODIFYING LIGNIN COMPOSITION AND INCREASING IN VIVO DIGESTIBILITY OF FORAGES

This application is a division of U.S. application No. 10/239,463, filed Feb. 20, 2003, now abandoned, which is a national stage application under 35 U.S.C. §371 of International Application No. PCT/US01/09398 filed Mar. 23, 2001, which application claims the benefit of U.S. Provisional Application No. 60/192,086 filed Mar. 24, 2000, which applications are herein incorporated by reference.

TECHNICAL FIELD OF INVENTION

This invention relates to a method of transforming plants, transformed plants and use thereof.

BACKGROUND OF THE INVENTION

Lignin is the major structural component of secondarily thickened plant cell walls. It is a complex polymer of hydroxylated and methoxylated phenylpropane units, linked via oxidative coupling that is probably catalyzed by both peroxidases and laccases (Boudet, et al. 1995. "Tansley review No. 80: Biochemistry and molecular biology of lignification," *New Phytologist* 129:203-236). Lignin imparts mechanical strength to stems and trunks, and hydrophobicity to water-conducting vascular elements. Although the basic enzymology of lignin biosynthesis is reasonably well understood, the regulatory steps in lignin biosynthesis and deposition remain to be defined (Davin, L. B. and Lewis, N. G. 1992. "Phenylpropanoid metabolism: biosynthesis of monolignols, lignans and neolignans, lignins and suberins," *Rec Adv Phytochem* 26:325-375).

There is considerable interest in the potential for genetic manipulation of lignin levels and/or composition to help improve digestibility of forages and pulping properties of trees (Dixon, et al. 1994. "Genetic manipulation of lignin and phenylpropanoid compounds involved in interactions with microorganisms," *Rec Adv Phytochem* 28:153178; Tabe, et al. 1993. "Genetic engineering of grain and pasture legumes for improved nutritive value," *Genetica* 90:181-200; Whetten, R. and Sederoff, R. 1991. "Genetic engineering of wood," *Forest Ecology and Management* 43:301-316). Small decreases in lignin content have been reported to positively impact the digestibility of forages (Casler, M. D. 1987. "In vitro digestibility of dry matter and cell wall constituents of smooth bromegrass forage," *Crop Sci* 27:931-934). By improving the digestibility of forages, higher profitability can be achieved in cattle and related industries. In forestry, chemical treatments necessary for the removal of lignin from trees are costly and potentially polluting.

Lignins contain three major monomer species, termed p-hydroxyphenyl (H), guaiacyl (G) and syringyl (S), produced by reduction of CoA thioesters of coumaric, ferulic and sinapic acids, respectively (see FIG. 1). In angiosperms, guaiacyl and syringyl units predominate, and the S/G ratio affects the physical properties of the lignin. The S and G units are linked through five different dimer bonding patterns (Davin, L. B. and Lewis, N. G. 1992. *Rec Adv Phytochem* 26:325-375). The mechanisms that determine the relative proportions of these linkage types in a particular lignin polymer are currently unknown. Furthermore, there is considerable debate as to whether lignin composition and structure are tightly controlled, or are flexible depending upon monomer availability (Lewis, N. G. 1999. "A 20th century roller coaster ride: a short account of lignification," *Current Opinion in Plant Biology* 2:153-162; Sederoff, et al. 1999. "Unexpected variation in lignin," *Current Opinion in Plant Biology* 2:145-152).

Lignin levels increase with progressive maturity in stems of forage crops, including legumes such as alfalfa (Jung, H. G. and Vogel, K. P. 1986. "Influence of lignin on digestibility of forage cell wall material," *J Anim Sci* 62:1703-1712) and in grasses such as tall fescue (Buxton, D. R. and Russell, J. R. 1988. "Lignin constituents and cell wall digestibility of grass and legume stems," *Crop Sci* 28:553-558). In addition, lignin composition changes with advanced maturity towards a progressively higher S/G ratio (Buxton, D. R. and Russell, J. R. 1988. *Crop Sci* 28:553-558). Both lignin concentration (Albrecht, et al. 1987. "Cell-wall composition and digestibility of alfalfa stems and leaves," *Crop Sci* 27:735-741; Casler, M. D. 1987. *Crop Sci* 27:931-934; Jung, H. G. and Vogel, K. P. 1986. *J Anim Sci* 62:1703-1712) and lignin methoxyl content, reflecting increased S/G ratio (Sewalt, et al. 1996. "Lignin impact on fiber degradation. 1. Quinone methide intermediates formed from lignin during in vitro fermentation of corn stover," *J Sci Food Agric* 71:195-203), have been reported to negatively correlate with forage digestibility for ruminant animals. Although a number of studies have linked decreased forage digestibility to increased S/G ratio as a function of increased maturity (Buxton, D. R. and Russell, J. R. 1988. *Crop Sci* 28:553-558; Grabber, et al. 1992. "Digestion kinetics of parenchyma and sclerenchyma cell walls isolated from orchardgrass and switchgrass," *Crop Sci* 32: 806-810), other studies have questioned the effect of lignin composition on digestibility (Grabber, et al. 1997. "p-hydroxyphenyl, guaiacyl, and syringyl lignins have similar inhibitory effects on wall degradability," *J Agric Food Chem* 45:2530-2532). Further, the hardwood gymnosperm lignins are highly condensed, essentially lacking S residues, and this makes them less amenable to chemical pulping, in apparent contradiction to the concept that reducing S/G ratio would be beneficial for forage digestibility. The reported lack of agreement in the relationship of lignin composition to forage digestibility and chemical pulping is partly due to the fact that the studies to date either have been in vitro, or have compared plant materials at different developmental stages, different varieties or even different species. Therefore, the development of isogenic lines that can be directly compared to reveal the effects of altered S/G ratio on forage digestibility would be beneficial.

The formation of the G and S units of lignin requires the activity of O-methyl-transferase enzymes. In angiosperms, the caffeic acid 3-O-methyltransferase (COMT) of lignin biosynthesis was originally described as being bifunctional, converting caffeic acid to ferulic acid and converting 5-hydroxyferulic acid to sinapic acid (Davin, L. B. and Lewis, N. G. 1992. *Rec Adv Phytochem* 26:325-375), as shown in FIG. 1. Methylation of the caffeate moiety also occurs at the level of the CoA thioester, catalyzed by caffeoyl CoA 3-O-methyltransferase (CCOMT) (Pakusch, et al., 1989, "S-adenosyl-L-methionine: trans-caffeoyl-coenzyme A 3-O-methyltransferase from elicitor-treated parsley cell suspension cultures," *Arch Biochem Biophys* 271:488-494). The involvement of the CCOMT enzyme in a parallel pathway to lignin monomer formation has been proposed (Ye, et al. 1994. "An alternative methylation pathway in lignin biosynthesis in *Zinnia*," *Plant Cell* 6:1427-1439; Zhong, et al. 1998. "Dual methylation pathways in lignin biosynthesis," *Plant Cell* 10:2033-2045). In vivo labeling studies in *Magnolia kobus* have shown that the methylation status of lignin monomers can also be determined at the level of the aldehyde or alcohol (Chen, et al. 1999. "Evidence for a novel biosynthetic pathway that regulates the ratio of syringyl to guaiacyl residues in lignin in the differentiating xylem of *Magnolia kobus* D C," *Planta* 207: 597-603). This is supported by the observation that the enzyme designated as ferulate 5-hydroxylase has a higher affinity for feruloyl aldehyde than for ferulic acid, at least in sweet gum (Osakabe, et al. 1999. "Coniferyl aldehyde 5-hydroxylation and methylation direct syringyl lignin biosynthesis in angiosperms," *Proc Natl Acad Sci USA* 96:8955-8960) and *Arabidopsis* (Humphreys, et al. 1999. "New routes for lignin biosynthesis defined by biochemical characterization of recombinant ferulate 5-hydroxylase, a multifunctional cytochrome P450-dependent monooxygenase," *Proc Natl Acad Sci USA* 96:10045-10050). Furthermore, 5-hydroxyconiferyl aldehyde has recently been shown to be a good substrate for COMT from various tree species (Li, et al. 2000. "5-Hydroxyconiferyl aldehyde modulates enzymatic methylation for syringyl monolignol formation, a new view of monolignol biosynthesis in angiosperms," *J Biol Chem* 275: 6537-6545). It has been reported that the inhibitory effect of 5-hydroxyconiferyl aldehyde on methylation of caffeate by COMT might prevent COMT from carrying out the first methylation step in the biosynthesis of S lignin (Li, et al. 2000. *J Biol Chem* 275:6537-6545). Thus, although studies of enzyme substrate specificities in vitro suggest that lignin monomers can be formed via the operation of a complex metabolic grid, involving O-methylation at multiple stages as shown in FIG. 1, whether this occurs in vivo has yet to be determined.

Several studies have addressed the properties of the O-methyltransferases involved in lignin biosynthesis in the world's major forage legume, alfalfa (*Medicago sativa* L.) (Gowri, et al. 1991. "Stress responses in alfalfa (*Medicago sativa* L.) X. Molecular cloning and expression of S-adenosyl-L-methionine: caffeic acid 3-O-methyltransferase, a key enzyme of lignin biosynthesis," *Plant Physiol* 97:7-14; Inoue, et al. 1998. "Developmental expression and substrate specificities of alfalfa caffeic acid 3-O-methyltransferase and caffeoyl CoA 3-O-methyltransferase in relation to lignification," *Plant Physiol* 117:761-770; Kersey, et al. 1999. "Immunolocalization of two lignin O-methyltransferases in stems of alfalfa (*Medicago sativa* L.)," *Protoplasma* 209:46-57). COMT from alfalfa expressed in *E. coli* shows preference (approximately 2:1) for 5-hydroxyferulic acid over caffeic acid, whereas CCOMT shows a similar degree of preference for caffeoyl CoA compared to 5-hydroxyferuolyl CoA (Inoue, et al. 1998. *Plant Physiol* 117:761-770). These studies suggest, but do not prove, that COMT may be involved preferentially in the formation of S lignin in alfalfa, and CCOMT in the formation of G lignin.

The substrate preference of COMT in crude alfalfa stem extracts changes with increasing internode maturity, in a manner consistent with the increase in lignin methoxyl group content with increasing maturity (Inoue, et al. 1998. *Plant Physiol* 117:761-770; Inoue, et al. 2000. "Substrate preferences of caffeic acid/5-hydroxyferulic acid 3-O-methyltransferases in developing stems of alfalfa (*Medicago sativa* L.)," *Arch Biochem Biophys* 375:175-182). Thus, in young internodes, the activity shows a preference for caffeic acid over 5-hydroxyferulic acid, whereas the opposite is true in the older internodes. An O-methyltransferase with preference for caffeic acid (COMT II) has recently been separated from the previously characterized COMT, and does not react with antisera recognizing the products of the previously characterized alfalfa COMT or CCOMT genes. This enzyme is most active against caffeic acid, for which it has a very low Km value (approximately 40-fold lower than lignification-associated COMT), but also methylates 5-hydroxyferulic acid, caffeoyl CoA, 5-hydroxyferuolyl CoA, quercetin and catechol (Inoue, et al. 2000. *Arch Biochem Biophys* 375:175-182). It is only present in young internodes and has disappeared by the fifth internode.

Tissue print hybridization analysis indicates that both COMT and CCOMT transcripts are localized to developing xylem elements in alfalfa stems, whereas CCOMT transcripts are also found in phloem (Inoue, et al. 1998. *Plant Physiology* 117:761-770). Immunolocalization studies at the light and electron microscope levels demonstrated expression of both COMT and CCOMT in the cytoplasm of alfalfa xylem parenchyma cells (Kersey, et al. 1999 *Protoplasma* 209:46-57). The presence of both enzymes in the same cells is consistent with the "metabolic grid" hypothesis for lignin monomer formation.

There have been several reports on the effects of down-regulation of COMT activity on lignin content and composition in transgenic tobacco and poplar (Ni, et al. 1994. "Reduced lignin in transgenic plants containing an engineered caffeic acid O-methyltransferase antisense gene," *Transgenic Res* 3:120-126; Atanassova, et al. 1995. "Altered lignin composition in transgenic tobacco expressing O-methyltransferase sequences in sense and antisense orientation," *Plant J* 8:465-477; Van Doorsselaere, et al. 1995. "A novel lignin in poplar trees with a reduced caffeic acid/5-hydroxy-ferulic acid O-methyltransferase activity," *Plant J* 8:855-864; Zhong, et al. 1998. *Plant Cell* 10:2033-2045). The results of these studies have been somewhat contradictory, possibly due to unspecified differences in tissue maturity, use of homologous versus heterologous transgenes, and use of different methods for lignin analysis. However, in cases where COMT has been reduced to levels below approximately 20% of wild-type by expression of a homologous transgene, a strong reduction in S/G ratio is accompanied by no apparent change in lignin content (Atanassova, et al. 1995. *Plant J* 8:465-477; Van Doorsselaere, et al. 1995. *Plant J* 8:855-864). In tobacco, down-regulation of CCOMT leads to a corresponding decrease in Klason lignin levels accompanied by decreases in the absolute levels of both S and G units (Zhong, et al. 1998. *Plant Cell* 10:2033-2045).

Most studies on genetic modification of lignin biosynthesis in transgenic plants have utilized the cauliflower mosaic virus 35S promoter to drive expression of sense or antisense lignification-associated genes (Halpin, et al. 1994. "Manipulation of lignin quality by down-regulation of cinnamyl alcohol dehydrogenase," *Plant J* 6:339-350; Ni, et al. 1994. *Transgenic Res* 3:120-126; Atanassova, et al. 1995. *Plant J* 8:465-477; Van Doorsselaere, et al. 1995. *Plant J* 8:855-864; Piquemal, et al. 1998. "Down-regulation of cinnamoyl-CoA reductase induces significant changes of lignin profiles in transgenic tobacco plants," *Plant J* 13:71-83; Zhong, et al. 1998. *Plant Cell* 10:2033-2045; Baucher, et al. 1999, "Down-regulation of cinnamyl alcohol dehydrogenase in transgenic alfalfa (*Medicago sativa* L.) and the effect on lignin composition and digestibility," *Plant Mol Biol* 39:437-447). However, more effective down-regulation may be obtained by driving expression of the transgene by a vascular-tissue specific promoter. For example, modification of lignin composition by overexpression of ferulate 5-hydroxylase in transgenic *Arabidopsis* was more effective if the transgene was driven by the lignification-associated *Arabidopsis* cinnamate 4-hydroxylase promoter than by the constitutive 35S promoter (Meyer, et al. 1998. "Lignin monomer composition is determined by the expression of a cytochrome P450-dependent monooxygenase in *Arabidopsis*," *Proc Natl Acad Sci USA* 95:6619-6623).

To date, there have been very few published reports on the genetic modification of lignin in forage crops, and most studies having concentrated on model systems such as *Arabidopsis* and tobacco, or tree species such a poplar. In one study, down-regulation of cinnamyl alcohol dehydrogenase, an enzyme later in the monolignol pathway than COMT or CCOMT, led to a small but significant improvement in in vitro dry matter digestibility in transgenic alfalfa (Baucher, et al. 1999. *Plant Mol Biol* 39:437-447). U.S. Pat. No. 5,451,514 discloses a method of altering the content or composition of lignin in a plant by stably incorporating into the genome of the plant a recombinant DNA encoding an mRNA having sequence similarity to cinnamyl alcohol dehydrogenase. U.S. Pat. No. 5,850,020 discloses a method for modulating lignin content or composition by transforming a plant cell with a DNA construct with at least one open reading frame coding for a functional portion of one of several enzymes isolated from *Pinus radiata* (pine) or a sequence having 99% homology to the isolated gene: cinnamate 4-hydroxylase (C4H), coumarate 3-hydroxylase (C3H), phenolase (PNL), O-methyltransferase (OMT), cinnamoyl-CoA reductase (CCR), phenylalanine ammonia-lyase (PAL), 4-coumarate:CoA ligase (4CL), and peroxidase (POX). U.S. Pat. No. 5,922,928 discloses a method of transforming and regenerating *Populus* species to alter the lignin content and composition using an O-methyltransferase gene. The question of how altering S/G ratio might affect digestibility of forage species is still unanswered.

It has now been found that transformation of plants with the lignin biosynthetic enzyme genes COMT or CCOMT in either a sense or antisense orientation under a lignification-associated tissue specific promoter, leading to the down-regulation of the corresponding homologous gene as well as reduced lignin content and modified lignin composition in the transgenic plants, results in significant improvements in forage digestibility, particularly in the case of CCOMT down-regulation.

SUMMARY OF THE INVENTION

In one aspect, the present invention is a method for modulating the lignin content of a forage legume comprising transforming a forage legume cell with a vector comprising a lignification-associated tissue specific promoter functionally linked to a DNA construct comprising at least one open reading frame encoding for either a caffeoyl CoA 3-O-methyltransferase enzyme or fragment thereof or a *Medicago sativa* caffeic acid 3-O-methyltransferase enzyme or fragment thereof; and generating plants from the transformed forage legume cell. In another embodiment, the forage legume cell is co-transformed with one vector comprising a lignification-associated tissue specific promoter functionally linked to a DNA construct comprising at least one open reading frame encoding for a caffeoyl CoA 3-O-methyltransferase enzyme or fragment thereof and another vector comprising a lignification-associated tissue specific promoter functionally linked to a DNA construct comprising at least one open reading frame encoding for a *Medicago sativa* caffeic acid 3-O-methyltransferase enzyme or fragment thereof. In yet another embodiment, a DNA construct comprising in tandem at least one open reading frame encoding for a caffeoyl CoA 3-O-methyltransferase enzyme or fragment thereof under expression control of a first lignification-associated tissue specific promoter and at least one open reading frame encoding for a *Medicago saliva* caffeic acid 3-O-methyltransferase enzyme or fragment thereof under expression control of a second lignification-associated tissue specific promoter, wherein said first and second lignification-associated tissue specific promoter can be the same or different, can be used in this method. The open reading frame can be in either a sense orientation or an antisense orientation. An exemplary lignification-associated tissue specific promoter is a bean PAL2 promoter.

In another aspect, the present invention is a method for producing a forage legume having altered lignin composition comprising transforming a forage legume cell with a DNA construct comprising either at least one open reading frame encoding for a caffeoyl CoA 3-O-methyltransferase enzyme or fragment thereof or a *Medicago sativa* caffeic acid 3-O-methyltransferase enzyme or fragment thereof under expression control of a lignification-associated tissue specific promoter to form a transgenic cell; and cultivating said transgenic cell under conditions conducive to regeneration and plant growth. In another embodiment, the forage legume cell is co-transformed with one DNA construct comprising at least one open reading frame encoding for a caffeoyl CoA 3-O-methyltransferase enzyme or fragment thereof under expression control of a lignification-associated tissue specific promoter and another DNA construct comprising at least one open reading frame encoding for a *Medicago sativa* caffeic acid 3-O-methyltransferase enzyme or fragment thereof under expression control of a lignification-associated tissue specific promoter. In yet another embodiment, a DNA construct comprising in tandem at least one open reading frame encoding for a caffeoyl CoA 3-O-methyltransferase enzyme or fragment thereof under expression control of a first lignification-associated tissue specific promoter and at least one open reading frame encoding for a *Medicago sativa* caffeic acid 3-O-methyltransferase enzyme or fragment thereof under expression control of a second lignification-associated tissue specific promoter, wherein said first and second lignification-associated tissue specific promoter can be the same or different, can be used in this method. The open reading frame can be in either a sense orientation or an antisense orientation. An exemplary lignification-associated tissue specific promoter is a bean PAL2 promoter.

In another aspect, the present invention is a method for improving the digestibility of forage legumes comprising stably incorporating into the genome of said forage legume a DNA construct comprising at least one open reading frame encoding for a 3-O-methyltransferase enzyme or a fragment thereof from the lignin biosynthetic pathway under expression control of a lignification-associated tissue specific promoter, wherein expression of the enzyme or enzyme fragment produces a change in lignin composition in the forage legume. One enzyme useful in this method is caffeoyl CoA 3-O-methyltransferase, which preferably causes a reduction in guaiacyl lignin content. In another embodiment, the forage legume is co-transformed with one DNA construct comprising at least one open reading frame encoding for a caffeoyl CoA 3-O-methyltransferase enzyme or fragment thereof under expression control of a lignification-associated tissue specific promoter and another DNA construct comprising at least one open reading frame encoding for a *Medicago sativa* caffeic acid 3-O-methyltransferase enzyme or fragment thereof under expression control of a lignification-associated tissue specific promoter. In yet another embodiment, a DNA construct comprising in tandem at least one open reading frame encoding for a caffeoyl CoA 3-O-methyltransferase enzyme or fragment thereof under expression control of a first lignification-associated tissue specific promoter and at least one open reading frame encoding for a *Medicago sativa* caffeic acid 3-O-methyltransferase enzyme or fragment thereof under expression control of a second lignification-associated tissue specific promoter, wherein said first and second lignification-associated tissue specific promoter can be the same or different, can be used in this method. The open reading frame can be in either a sense orientation or an antisense orientation. An exemplary lignification-associated tissue specific promoter is a bean PAL2 promoter.

In another aspect, the present invention is a method for producing a woody plant having altered lignin composition comprising transforming a woody plant cell with a DNA construct comprising at least one open reading frame encoding for a *Medicago sativa* caffeoyl CoA 3-O-methyltransferase enzyme or a *Medicago sativa* caffeic acid 3-O-methyltransferase enzyme or fragment thereof under expression control of a lignification-associated tissue specific promoter to form a transgenic cell; and cultivating the transgenic cell under conditions conducive to regeneration and plant growth. In another embodiment, the woody plant cell is co-transformed with one DNA construct comprising at least one open reading frame encoding for a caffeoyl CoA 3-O-methyltransferase enzyme or fragment thereof under expression control of a lignification-associated tissue specific promoter and another DNA construct comprising at least one open reading frame encoding for a *Medicago sativa* caffeic acid 3-O-methyltransferase enzyme or fragment thereof under expression control of a lignification-associated tissue specific promoter. In yet another embodiment, a DNA construct comprising in tandem at least one open reading frame encoding for a caffeoyl CoA 3-O-methyltransferase enzyme or fragment thereof under expression control of a first lignification-associated tissue specific promoter and at least one open reading frame encoding for a *Medicago sativa* caffeic acid 3-O-methyltransferase enzyme or fragment thereof under expression control of a second lignification-associated tissue specific promoter, wherein said first and second lignification-associated tissue specific promoter can be the same or different, can be used in this method. The open reading frame can be in either a sense orientation or an antisense orientation. An exemplary lignification-associated tissue specific promoter is a bean PAL2 promoter.

In another aspect, the present invention is a method for modulating the lignin content of a woody plant comprising transforming a woody plant cell with a DNA construct comprising at least one open reading frame encoding for a *Medicago sativa* caffeoyl CoA 3-O-methyltransferase enzyme or a *Medicago sativa* caffeic acid 3-O-methyltransferase enzyme or fragment thereof under expression control of a lignification-associated tissue specific promoter to form a transgenic cell; and cultivating the transgenic cell under conditions conducive to regeneration and plant growth. In another embodiment, the woody plant cell is co-transformed with one DNA construct comprising at least one open reading frame encoding for a caffeoyl CoA 3-O-methyltransferase enzyme or fragment thereof under expression control of a lignification-associated tissue specific promoter and another DNA construct comprising at least one open reading frame encoding for a *Medicago sativa* caffeic acid 3-O-methyltransferase enzyme or fragment thereof under expression control of a lignification-associated tissue specific promoter. In yet another embodiment, a DNA construct comprising in tandem at least one open reading frame encoding for a caffeoyl CoA 3-O-methyltransferase enzyme or fragment thereof under expression control of a first lignification-associated tissue specific promoter and at least one open reading frame encoding for a *Medicago sativa* caffeic acid 3-O-methyltransferase enzyme or fragment thereof under expression control of a second lignification-associated tissue specific promoter, wherein said first and second lignification-associated tissue specific promoter can be the same or different, can be used in this method. The open reading frame can be in either a sense orientation or an antisense orientation. An exemplary lignification-associated tissue specific promoter is a bean PAL2 promoter.

In another aspect, the present invention is a method for making lignins with altered dimer bonding patterns comprising transforming a plant cell with a DNA construct comprising at least one open reading frame encoding for a caffeoyl CoA 3-O-methyltransferase enzyme or a caffeic acid 3-O-methyltransferase enzyme or a fragment thereof under expression control of a lignification-associated tissue specific promoter to form a transgenic cell; and cultivating the transgenic cell under conditions conducive to regeneration and plant growth. In another embodiment, the plant cell is co-transformed with one DNA construct comprising at least one open reading frame encoding for a caffeoyl CoA 3-O-methyltransferase enzyme or fragment thereof under expression control of a lignification-associated tissue specific promoter and another DNA construct comprising at least one open reading frame encoding for a *Medicago sativa* caffeic acid 3-O-methyltransferase enzyme or fragment thereof under expression control of a lignification-associated tissue specific promoter. In yet another embodiment, a DNA construct comprising in tandem at least one open reading frame encoding for a caffeoyl CoA 3-O-methyltransferase enzyme or fragment thereof under expression control of a first lignification-associated tissue specific promoter and at least one open reading frame encoding for a *Medicago sativa* caffeic acid 3-O-methyltransferase enzyme or fragment thereof under expression control of a second lignification-associated tissue specific promoter, wherein said first and second lignification-associated tissue specific promoter can be the same or different, can be used in this method. The open reading frame can be in either a sense orientation or an antisense orientation. An exemplary lignification-associated tissue specific promoter is a bean PAL2 promoter.

In yet another aspect, the present invention is a plant transformed by any of the methods disclosed herein.

FIG. 3A-3J depict COMT or CCOMT activities in stem tissue of control lines and COMT and/or CCOMT transgenic lines. FIG. 3A shows COMT activity in control plants transformed with empty pCAMBIA3300 vector. FIG. 3B shows COMT activity in plants transformed with COMT in the sense orientation ("SC"). FIG. 3C shows COMT activity in plants transformed with a construct containing both COMT and CCOMT in the sense orientation ("DS"), or by co-transformation with individual antisense COMT and CCOMT constructs. FIG. 3D shows COMT activity in plants transformed with COMT in the antisense orientation ("AC"). FIG. 3E shows COMT activity in plants transformed with a construct containing both COMT and CCOMT in the antisense orientation ("DA"), or by co-transformation with individual antisense COMT and CCOMT constructs. FIG. 3F shows CCOMT activity in control plants transformed with empty pCAMBIA3300 vector. FIG. 3G shows CCOMT activity in plants transformed with CCOMT in the sense orientation ("SCC"). FIG. 3H shows CCOMT activity in plants transformed with a construct containing both COMT and CCOMT in the sense orientation ("DS"), or by co-transformation with individual antisense COMT and CCOMT constructs. FIG. 3I shows CCOMT activity in plants transformed with CCOMT in the antisense orientation ("ACC"). FIG. 3J shows CCOMT activity in plants transformed with a construct containing both COMT and CCOMT in the antisense orientation ("DA"), or by co-transformation with individual antisense COMT and CCOMT constructs. The bars represent the means (solid lines) and standard deviations (dashed lines) of the respective control populations. Enzyme activities were determined in the $6^{th}$-$9^{th}$ internodes of stems of identical developmental stage.

Figure 4:
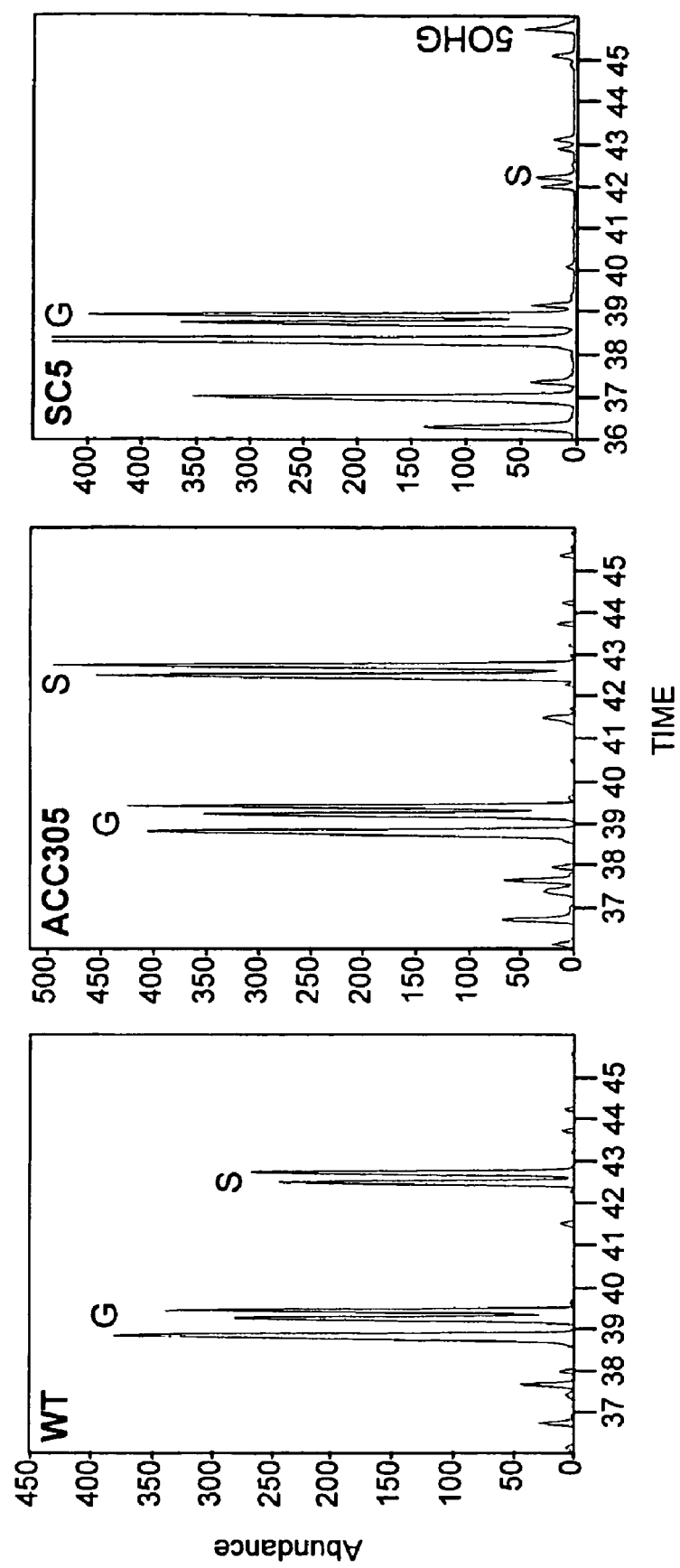

FIG. 4 depicts typical gas chromatographs showing thioacidolysis products from lignin samples of wild-type (WT), COMT-suppressed (SC5), and CCOMT-suppressed (ACC305) alfalfa plants. G, S and 5-hydroxyguaiacyl (5OHG) units are marked. The peaks appear as doublets because of the formation of erythro and threo isomers of each degradation product.

FIG. 5 depicts the full nucleotide sequence for the 1097 by coding region of alfalfa COMT (nucleotides 31-1128 of GenBank Accession No. M63853 (SEQ ID NO:3)).

FIG. 6 depicts the full nucleotide sequence for the 743 by coding region of alfalfa CCOMT (nucleotides 36-779 of GenBank Accession No. U20736 (SEQ ID NO:1)).

DETAILED DESCRIPTION

Using the methods of the present invention, the lignin content and composition of a forage legume such as alfalfa can be modified. Forage legumes are transformed with genes encoding O-methyltransferase (OMT) enzymes from the lignin biosynthetic pathway inserted in the sense or antisense orientations and under a lignification-associated tissue specific promoter. This transformation method can result in a variety of outcomes: a down-regulation of the corresponding homologous OMT genes, gene silencing, reduced OMT activity levels, reduced lignin content, and modified lignin composition in transgenic plants, and increased digestibility of transgenic plant materials in ruminant animals. Transforming forage legumes with OMT enzymes has now made it possible to produce plants having modified lignin content and composition for direct comparison of the effects of lignin content and/or composition on forage digestibility. A preferred embodiment of the invention includes genetically engineering forage varieties with modified lignin to increase forage digestibility in animals. In another embodiment, plants are modified to alter lignins and improve pulping characteristics for the paper industry.

Transformation methods of the present invention utilize binary constructs comprising DNA sequences encoding O-methyltransferase (OMT) enzymes from the lignin biosynthetic pathway, preferably in conjunction with a gene promoter sequence and a gene termination sequence. In the present invention, full or partial DNA sequences either isolated from alfalfa or produced by recombinant means and encoding or partially encoding O-methyltransferase (OMT) enzymes, are used in the transformation process. Preferably, a full length alfalfa COMT or CCOMT cDNA sequence in the sense or antisense orientation is placed in a binary vector with the cDNA being driven by a lignification-associated promoter. Alternatively, constructs can contain tandem COMT and CCOMT cDNAs in sense or antisense orientations, with each cDNA being driven independently by a lignification-associated promoter. While full length COMT and CCOMT cDNA sequences are preferred, a genomic DNA sequence or a cDNA sequence encoding a portion of COMT or CCOMT can be used in the present invention, provided that the DNA sequence is of sufficient length so as to encode a fragment of the enzyme wherein the fragment is effective for causing antisense inhibition or gene silencing of OMT expression.

To drive expression of transgenes in forage legumes, a lignification-associated promoter is utilized. Any lignification-associated promoter known in the art can be useful in the present invention. However, since COMT and CCOMT enzymes are expressed in the xylem and phloem parenchyma in alfalfa, lignification-associated promoters selective for vascular tissue are preferred. The promoter gene sequence can be endogenous to the target plant, or it can be exogenous provided that the promoter is functional in the target plant. A lignification-associated tissue specific promoter can be used to target the production of sense or antisense RNA in the tissue of interest. An exemplary gene promoter sequence for use in forage legumes is the bean (*Phaseolus vulgaris*) PAL2 promoter.

Many gene termination sequences known in the art are useful in the present invention. The gene termination sequence can be from the same gene as the gene promoter sequence or from a different gene. An exemplary gene terminator sequence is the 3' end of the nopaline synthase, or nos, gene.

The DNA constructs of the present invention can optionally contain any selection marker effective in plant cells as a means of detecting successful transformation. Exemplary selection markers include antibiotic or herbicide resistance genes. Preferred selectable markers include a neomycin phosphotransferase gene or phosphinothricin acetyl transferase (bar) gene. For example, a preferable selection marker is the bar gene encoding phosphinothricin acetyl transferase which confers resistance to phosphinothricin-based herbicides.

Transformation methods of the present invention include any means known in the art by which forage legumes can be successfully transformed using the DNA constructs disclosed herein. *Agrobacterium*-mediated transformation by leaf disk or biolistic techniques followed by regeneration through somatic embryogenesis, direct organogenesis, or vacuum infiltration techniques that by-pass the need for tissue culture, are preferred.

EXAMPLE 1

Lignin Modification of Alfalfa

Alfalfa plants were successfully transformed using the lignin-modifying transformation methods of the present invention. Alfalfa plants exhibiting changes in both lignin content and composition were obtained.

To drive expression of transgenes in forage legumes, we chose the bean PAL2 promoter, which was previously characterized as associated with lignification and strongly expressed in the vascular tissue of transgenic tobacco (Leyva, et al. 1992. "Cis-element combinations determine phenylalanine ammonia-lyase gene tissue specific expression patterns," *Plant Cell* 4:263-271; Shufflebottom, et al. 1993. "Transcription of two members of a gene family encoding phenylalanine ammonia-lyase leads to remarkably different cell specificities and induction patterns," *Plant J* 3:835-845). A number of gene constructs were made, either to test the tissue specificity of the bean PAL2 promoter in alfalfa using the reporter gene GUS, or to drive expression of the alfalfa O-methyltransferase genes COMT and/or CCOMT in the sense or antisense orientations. The bean PAL2 promoter was obtained from the genomic clone gPAL2 (Cramer, et al. 1989. "Phenylalanine ammonia-lyase gene organization and structure," *Plant Mol Biol* 12:367-383) and was cloned into the EcoRI/BamHI sites of pUC18. Site-directed mutagenesis was used to delete the NdeI site in pUC18 to create the plasmid pUC18-PAL. The GUS open reading frame was excised from the plasmid pGN100 (Reimann-Philipp, R. and Beachy, R. N. 1993. "Coat protein-mediated resistance in transgenic tobacco expressing the tobacco mosaic virus coat protein from tissue-specific promoters," *Mol Plant Microbe Interact* 6:323-330) by EcoRI/SmaI digestion, and two DNA polylinkers containing different restriction sites, EcoRI-Bg/II-NdeI-BamHI-SmaI and EcoRI-BglII-BamHI-NdeI-SmaI, were introduced independently between the EcoRI and SmaI sites, respectively. A BglII/PstI fragment containing the nopaline synthase (nos) terminator sequence was inserted into the BamHI/PstI sites of pUC18-PAL to give the plasmids pPTN1 and pPTN2, which contain the bean PAL2 promoter and nos terminator. To create the cassette for gusA gene expression, the bean PAL2 promoter was released from the plasmid pPTN2 by digestion with EcoRI, and the ends were filled in with Klenow fragment and then digested with BamHI. The plasmid ubi3-GUS (Garbarino J. E. and Belknap W. R. 1994. "Isolation of a ubiquitin-ribosomal protein gene (ubi3) from potato and expression of its promoter in transgenic plants," *Plant Mol Biol* 24:119-127) was treated with XbaI, Klenow, and BamHI to replace the ubi3 promoter with the isolated bean PAL2 promoter. The gusA expression cassette was then cloned into HindIII/EcoRI cut pCAMB 13 300 to create the gusA expression construct pCAMGUS.

Constructs were introduced into *Agrobacterium tumefaciens* LBA4404 using the Gibco BRL Lifetechnologies electroporation procedure (Gibco BRL Lifetechnologies, Rockville, Md.). Leaf disc transformation of alfalfa (cv Regen SY) was performed based on a method described previously (Shahin, et al. 1986 "Transformation of cultivated alfalfa using disarmed *Agrobacterium tumefaciens*," *Crop Sci* 26:1235-1239; Thomas, et al. 1990. "Selection of interspecific somatic hybrids of *Medicago* by using *Agrobacterium*-transformed tissues," *Plant Sci* 69:189-198). Phosphinothricin (5 mg/L) was added to the culture medium for selection of resistant transformants. Alfalfa plants were grown in the greenhouse under standard conditions. All transformations were performed with clonally propagated material of one selected highly regenerable line named 4D.

Figure 1A:
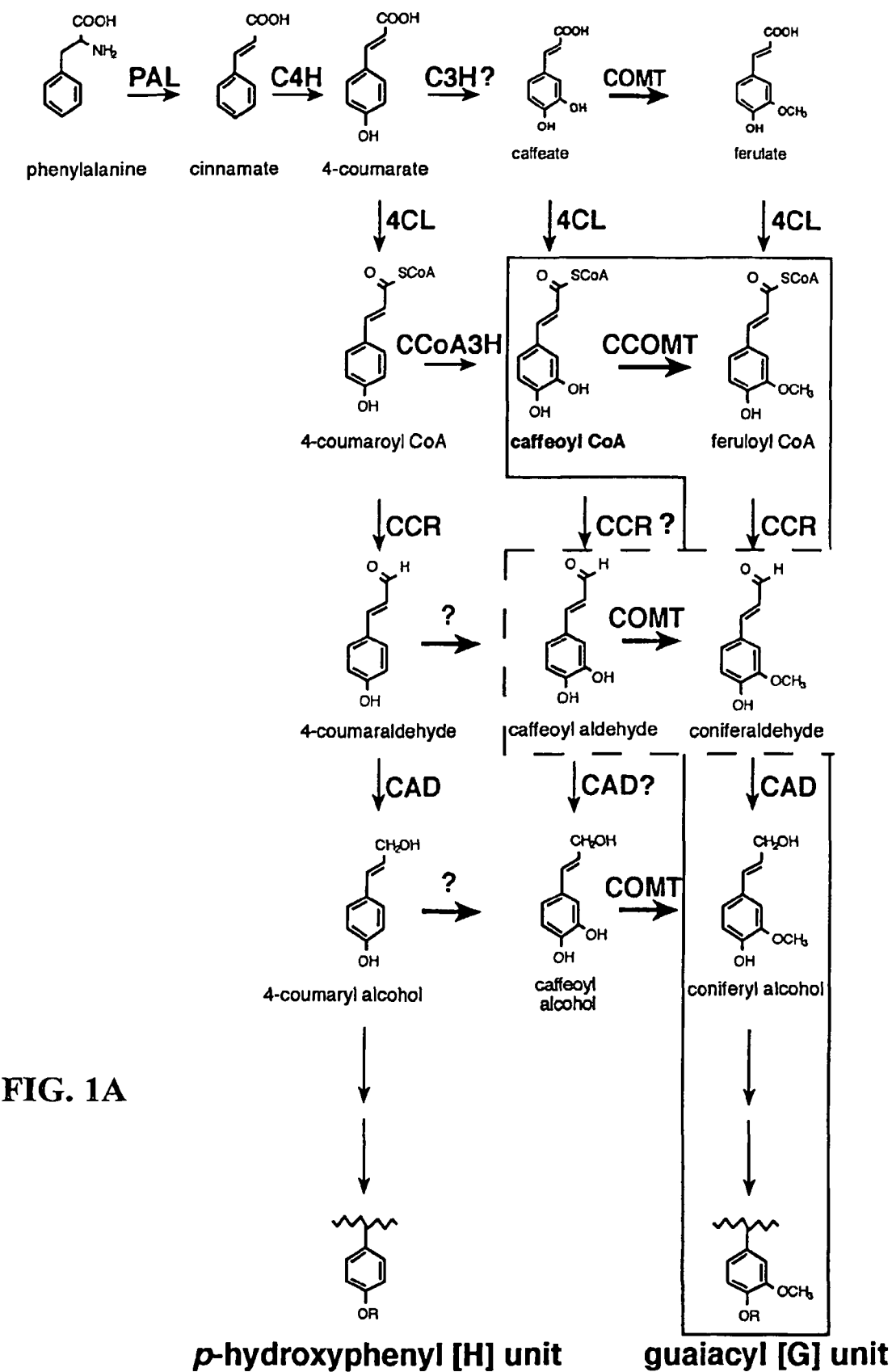
FIGS. 1A and 1B depict proposed biochemical pathways to lignin monomers. The "metabolic grid" shown in this scheme incorporates the results of recent studies suggesting previously unexpected substrate specificities for ferulate 5-hydroxylase (F5H) and COMT (Humphreys, et al. 1999. *Proc Natl Acad Sci USA* 96:10045-10050; Osakabe, et al. 1999 *Proc Natl Acad Sci USA* 96:8955-8960; Li, et al. 2000. *J Biol Chem* 275:6537-6545).
Figure 1B:
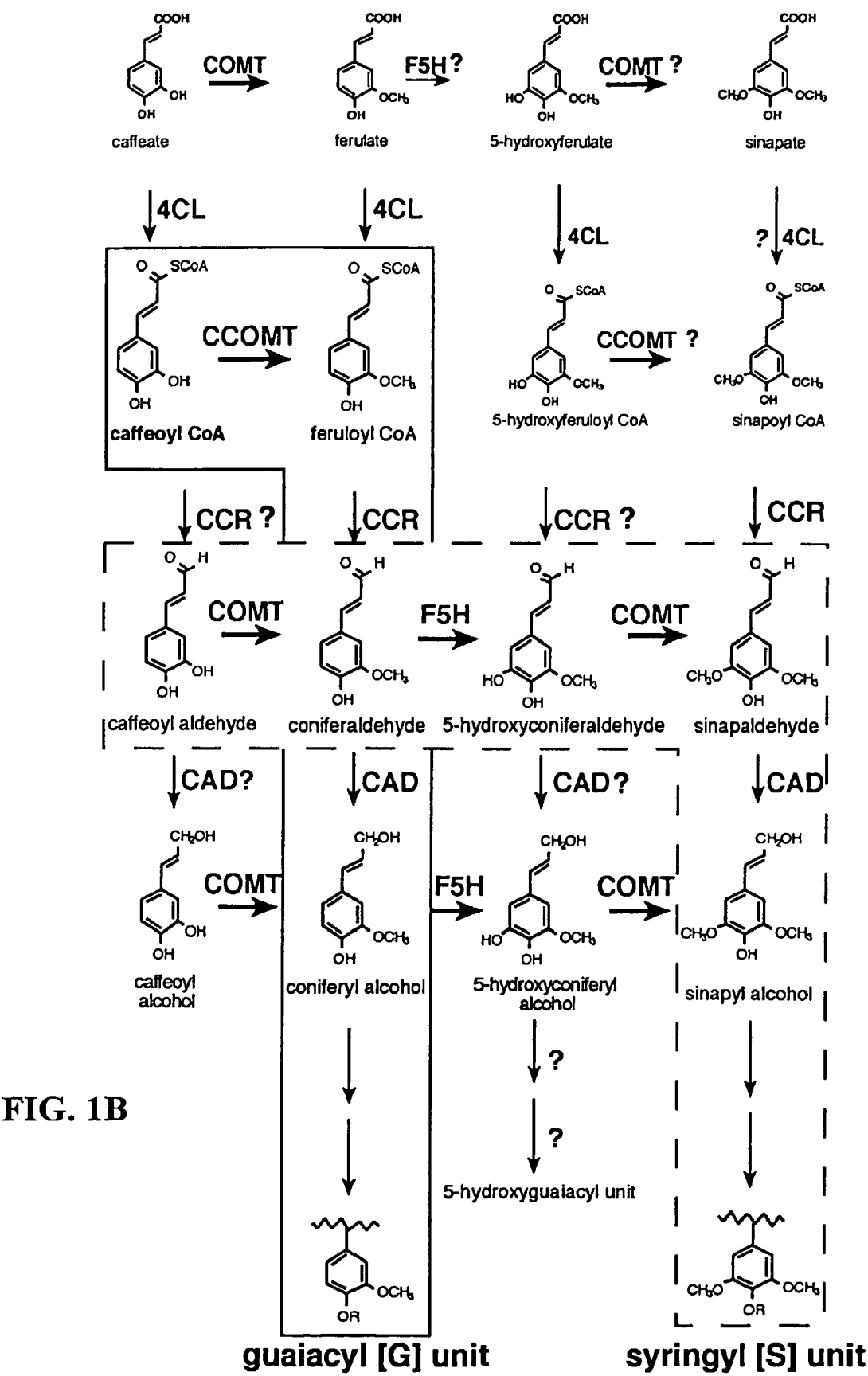
Figure 2:
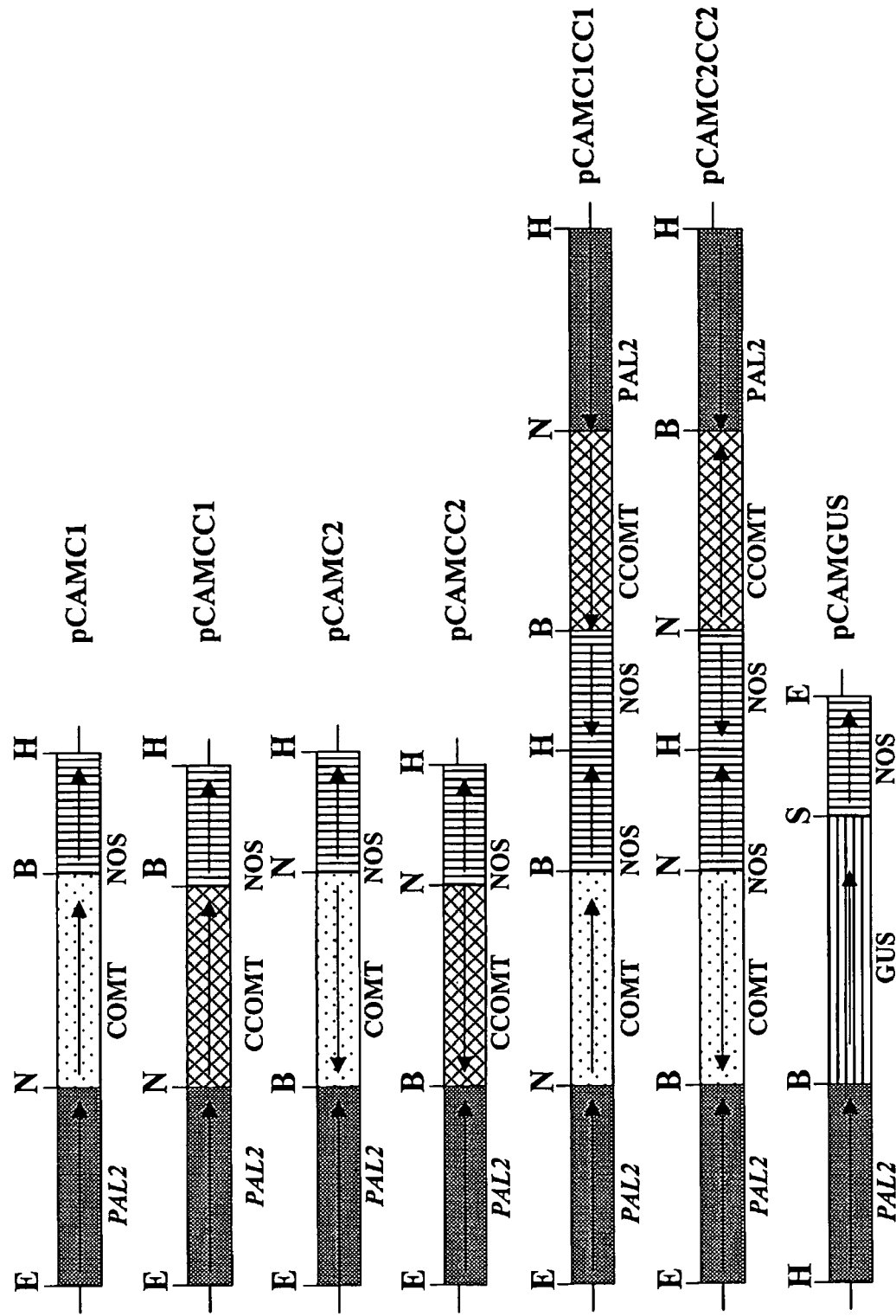
FIG. 2 depicts binary constructs used for genetic modification of COMT and CCOMT expression in transgenic alfalfa. PAL2 is the bean phenylalanine ammonia-lyase PAL2 promoter from −183 to −1226 bp (Liang, et al. 1989. "Developmental and environmental regulation of a phenylalanine ammonia-lyase 13-glucuronidase gene fusion in transgenic tobacco plants." *Proc Natl Acad Sci USA* 86:9284-9288) and NOS, the nopaline synthase terminator. Directionality of COMT and CCOMT is indicated by the arrows relative to the direction of the PAL2 promoter. Constructs containing both COMT and CCOMT in sense or antisense orientations were made by duplication of the PAL2/COMT/NOS and PAL2/CCOMT/NOS cassettes, and therefore, each cDNA is under control of a separate PAL2 promoter. Introduction of both transgenes into a single plant was also achieved by co-transformation (Irdani, et al. 1998. "Construction of a new vector conferring methotrexate resistance in *Nicotiana tabacum* plants," *Plant Mol Biol* 37:1079-1084) with single COMT and CCOMT constructs. All constructs are in the binary vector pCAMBIA3300.

To confirm tissue specificity of the bean PAL2 promoter in transgenic alfalfa, several independent plants were generated via *Agrobacterium*-mediated transformation with the pCAMGUS binary vector containing the GUS marker gene under control of the full length (-182 to -1226 bp) bean PAL2 promoter, as illustrated in FIG. 2. Histochemical GUS assays were then performed to determine the cellular sites of PAL2 promoter activity. Hand sections of alfalfa stems, roots, and petioles were incubated on ice for 30 minutes in 2% paraformaldehyde and 100 mM Na-phosphate buffer, pH 7.0. They were then vacuum infiltrated in 2 mM X-gluc in 50 mM Na-phosphate buffer, pH 7.0, 0.5% Triton X-100 for 10 seconds, followed by a 2 hour incubation at 37° C. After staining, green tissues were bleached in 70% ethanol several times to allow visualization of the blue staining. Transverse sections from these plants (containing the PAL2-GUS construct pCAMGUS) stained blue with the chromogenic substrate X-gluc revealed GUS expression in the vascular tissue of roots, stems, and petioles that was absent from similarly stained non-transgenic control tissue (containing empty pCAMBIA3300 vector). Although the majority of the staining in stem and petiole tissue was localized to vascular parenchyma cells, there was also some staining of mesophyll cells and epidermal cells of petioles. These results were reproduced in other independent transformants. The relatively selective vascular tissue staining indicated that the bean PAL2 promoter would be suitable for directing expression of COMT and CCOMT sense and antisense transgenes, as these enzymes are expressed in xylem and phloem parenchyma in alfalfa (Kersey, et al. 1999. *Protoplasma* 209:46-57).

Full length alfalfa COMT and CCOMT cDNA sequences in the sense and antisense orientations were placed under control of the bean PAL2 promoter in the binary vector pCAMBIA3300, as summarized in FIG. 2. Additional constructs contained tandem COMT and CCOMT cDNAs, in the sense or antisense orientations, with each cDNA driven independently by a bean PAL2 promoter, as shown in FIG. 2. The COMT and CCOMT coding sequences were isolated from separate OMT cDNA constructs in pET vectors (Inoue, et al. 1998. *Plant Physiol* 117:761-770), which contained the 1097 by full length alfalfa COMT cDNA (Gowri, et al. 1991. *Plant Physiol* 97:7-14; GenBank Accession No. M63853) (SEQ ID NO:3 and FIG. 5) or the 743 by full length alfalfa CCOMT cDNA (GenBank Accession No. U20736) (SEQ ID NO: 1 and FIG. 6). The COMT and CCOMT inserts were removed as NdeI/BamHI fragments and ligated into the NdeI/BamHI sites of pPTN1 and pPTN2, resulting in plasmids pPTNI-COMT and pPTNI-CCOMT for sense expression of COMT or CCOMT, respectively, and pPTN2-COMT and pPTN2-CCOMT for antisense expression of COMT or CCOMT, respectively. The chimeric genes were then cloned as EcoRI/HindIII fragments into the EcoRI/HindIII sites of the binary vector pCAMBIA3300, which has a phosphinothricin resistance gene as selectable marker. Resulting binary constructs were designated pCAMC1 (single COMT, sense), pCAMC2 (single COMT, antisense), pCAMCCI (single CCOMT, sense), pCAMCC2 (single CCOMT, antisense), pCAMCICC1 (tandem COMT sense, CCOMT sense), pCAMC2CC2 (tandem COMT antisense, CCOMT antisense), and pCAMGUS, as shown in FIG. 2.

To make constructs for sense or antisense expression of tandem COMT and CCOMT genes, plasmids pPTN1-COMT and pPTN2-COMT were first cut with EcoRI, filled in with the Klenow fragment of DNA polymerase I, and then digested with HindIII. The isolated fragments were ligated into NarI-treated, Klenow-treated, and HindIII-treated pPTN1 to create the shuttle vector pPTN1-D. The tandem COMT and CCOMT region together with the PAL2 promoter and nos terminator was cut out with AatII, filled in with Klenow, digested with EcoRI and finally ligated into SmaI/EcoRI cut pCAMBIA3300 to give binary expression constructs with both OMTs in the sense or antisense orientation. These were designated pCAMC1CC1 (tandem COMT sense, CCOMT sense) and pCAMC2CC2 (tandem COMT antisense, CCOMT antisense). Introduction of both COMT and CCOMT transgenes into the same plant was also achieved by co-transformation using the above single COMT and CCOMT constructs. Constructs were introduced into alfalfa by *Agrobacterium*-mediated transformation of leaf discs followed by regeneration through somatic embryogenesis.

After regeneration (Thomas, et al. 1990. Plant Science 69:189-198) and transfer to the greenhouse, plants were first analyzed for integration of COMT and CCOMT transgenes by polymerase chain reaction (PCR). The primers used were 5'-GGGTTCAACAGGTGAAACTC-3' (SEQ ID NO: 5) and 5'-CCTTCTTAAGAAACTCCATGATG-3' (SEQ ID NO:6) for COMT, and 5'-GGCAACCAACGAAGATCAAAAGC-3' (SEQ ID NO:7) and 5'-CTTGATCCTACGGCAGATAGT-GATTCC-3' (SEQ ID NO:8) for CCOMT, which yielded diagnostic 1.1 kb or 0.75 kb amplification products in COMT or CCOMT transformants respectively. Approximately 80% of the plants surviving selection were PCR-positive.

Internode samples ($6^{th}$-$9^{th}$ internodes) from stems of putative transformants at the same developmental stage were harvested and assayed for COMT and CCOMT enzymatic activity, as shown in FIG. 3. Younger internodes ($1^{st}$-$4^{th}$) were excluded from the tissue used for enzyme analysis, because these contain a second form of COMT that is not recognized by the antiserum raised against the alfalfa COMT targeted by the present transgenic strategy (Inoue, et al. 2000. *Arch Biochem Biophys* 375:175-182). Alfalfa stems (internodes 6-9, counting from the first fully opened leaf at the top) were collected and homogenized in liquid nitrogen. Powdered tissue was extracted for 1 hour at 4° C. in extraction buffer (100 mM Tris-HCl, pH 7.5, 10% glycerol, 2 mM DTT, 0.2 mM $MgCl_2$, 1 mM PMSF), and desalted on PD-10 columns (Pharmacia, Piscataway, N.J.). Protein concentrations were determined using Bradford dye-binding reagent (Bio-Rad) with bovine serum albumin (BSA) as a standard. Enzyme activities were assayed essentially as described elsewhere (Gowri, et al. 1991. *Plant Physiol* 97:7-14; Ni, et al. 1996. "Stress responses in alfalfa (*Medicago sativa* L.) XXI. Activation of caffeic acid 3-O-methyltransferase and caffeoyl CoA 3-O-methyltransferase genes does not contribute to changes in metabolite accumulation in elicitor-treated cell suspension cultures," *Plant Physiol* 112:117-726) with the following modifications. The assay mixtures contained 5 µl of [$^{14}CH_3$]-S-adenosyl-L-Met (0.6 mM, 13 µCi/µmol), 5 µl of caffeic acid (1 mM) or caffeoyl CoA (1 mM), 30 µl of assay buffer (100 mM Tris-HCl, pH 7.5, 10% glycerol, 2 mM DTT, 0.2 mM $MgCl_2$), and 5 µl protein extract. They were incubated at 30° C. for 30 minutes, stopped by adding 50 µl of 0.2 M HCl (for COMT) or 10 µl of 3 M NaOH for CCOMT, incubated at 37° C. for 10 minutes, then (for CCOMT) acidified by adding 40 µl of 1 M HCl. Labeled ferulic acid was extracted into 200 µl of hexane:ethyl acetate (1:1, v/v), and 150 µl of the separated organic phases were transferred to scintillation vials for determination of radioactivity.

There was a wide variation (nearly 4-fold) in COMT activity in a control population of 20 independent plants transformed with empty pCAMBIA3300 vector, as seen in FIG. 3A. Of twenty transformants containing the single COMT sense sequence shown in FIG. 3B, three lines (SC4, SC5, and SC52) had strongly reduced COMT activities, whereas the remainder of the population exhibited, on average, a small increase in COMT activity compared to the average value for the control population. A similar situation was seen with respect to COMT activity in the double sense transformants shown in FIG. 3C, with one plant (DS14) showing strongly down-regulated COMT activity and the remainder of the population having a slightly elevated average COMT activity compared to the controls. In the COMT antisense population shown in FIG. 3D, a single plant (AC310) had strongly reduced COMT activity, with the remainder of the overall population showing on average a small reduction when compared to the average value for the control population. In the double antisense lines (FIG. 3E), one plant (DA302) showed strongly reduced COMT activity.

There was less variation in CCOMT than in COMT activity in the control population, as seen by a comparison of FIG. 3A and FIG. 3F. Otherwise, the pattern of CCOMT activities in the transformants harboring sense and antisense CCOMT constructs was very similar to that observed for COMT. CCOMT activity was strongly down-regulated in two CCOMT sense lines (SCC 19 and SCC 20) as shown in FIG. 3G, in one double sense line (DS 14) as shown in FIG. 3H, in two antisense lines (ACC305 and ACC315) as shown in FIG. 3I) and in one double COMT/CCOMT antisense line (DA302) as shown in FIG. 3J.

Transgene insertion was confirmed in selected COMT and CCOMT down-regulated alfalfa lines by Southern blot analysis. Total DNA was isolated from leaf tissue of each alfalfa line using a nucleon phytopure plant DNA extraction kit (Amersham; Arlington Heights, Ill.). DNA samples (7 µg) were digested with EcoRI, electrophoretically separated, and transferred to a nylon membrane (Hybond-N, Amersham) by standard procedures (Sambrook, et al. 1989. *Molecular Cloning. A Laboratory Manual,* 2nd Ed., New York, Cold Spring Harbor Laboratory Press). Blots were probed with $^{32}$P-labeled 1.1 kb alfalfa COMT or 0.75 kb CCOMT coding sequence probe and washed at high stringency conditions (final wash 0.1×SSC, 0.1% SDS, 65° C.). The probe was labeled with a $^{32}$P-dCTP labeling kit (Amersham). A comparison of the results for selected control and COMT and/or CCOMT down-regulated transgenic lines showed transgene integration patterns indicative of multiple transgene insertions of COMT in independent transformants: SC4 (single COMT sense), SC5 (single COMT sense), DS14 (double sense), DA302 (double antisense), and AC310 (single COMT antisense), all showing 3-5 unique bands. Similar transgene integration patterns were obtained showing multiple transgene insertions of CCOMT in independent transformants: DA302 (double antisense), ACC305 and ACC315 (single CCOMT antisense), and DS14 (double sense), all showing 1-5 unique bands.

RNA gel blot analysis confirmed that the reduced COMT or CCOMT activity in the various lines resulted from a severe reduction in COMT or CCOMT transcript levels. RNA was prepared from alfalfa leaves using TRIREAGENT (Molecular Research Center, Inc.) according to the manufacturer's suggested protocol. Total RNA samples (5-10 µg) were fractionated on a formaldehyde denaturing gel according to standard protocols (Sambrook, et al. 1989. *Molecular Cloning. A*

*Laboratory Manual*, 2nd Ed., New York, Cold Spring Harbor Laboratory Press), transferred to a Hybond-N nylon membrane, and hybridized with radiolabeled full length alfalfa COMT or CCOMT cDNA sequences at high stringency as for DNA gel blots. COMT transcripts were almost undetectable in the total RNA fraction from sense lines SC4, SC5, antisense line AC310, the double sense line DS14 and the double antisense line DA302. CCOMT transcripts were likewise virtually undetectable in antisense lines ACC305 and ACC315, and in the double antisense line DA302. However, CCOMT transcripts were relatively unaffected in the double sense line DS14, in which CCOMT activity is reduced to approximately 23% of wild type.

Comparisons of COMT and CCOMT protein levels in the various transgenic lines were carried out by western blot analysis. Crude proteins were extracted from the $6^{th}$ to $9^{th}$ internodes of selected individual transformants and two wild type plants, separated on 8-12% gradient SDS-polyacrylamide gels and electrotransferred onto nitrocellulose membranes. The membranes were incubated in blocking buffer (PBS containing 0.05% Tween 20 and 5% skim milk) for 2 hours, then incubated in blocking buffer with monospecific polyclonal antisera raised against recombinant alfalfa COMT or CCOMT proteins for 2 hours (Kersey, et al. 1999. *Protoplasma* 209:46-57). The signals were detected with ECL Western blotting detection reagents (Amersham) according to the manufacturer's protocol. The results indicated almost complete loss of COMT protein in the sense lines SC4, SC5 and SC52, in the antisense line AC310, in the double antisense line DA302, and in the double sense line DS14. CCOMT protein levels were almost undetectable in the antisense lines ACC305 and ACC315, and were strongly reduced in the double antisense line DA302 and the double sense line DS14. Complete loss of CCOMT protein in the CCOMT antisense line ACC305 was unexpectedly accompanied by a strong increase in COMT protein level, and in COMT enzymatic activity (Table I). The above results indicate that expression of OMT sequences from the bean PAL2 promoter results in greater down-regulation of COMT and CCOMT than obtained in previous studies (Ni, et al. 1994. Transgenic Res 3:120-126; Atanassova, et al. 1995. *Plant J* 8:465-477; Van Doorsselaere, et al. 1995. *Plant J* 8:855-864; Zhong, et al. 1998. *Plant Cell* 10:2033-2045).

Reduction of enzymatic activity resulting from reduced transcript levels in plants expressing gene constructs in the sense orientation is characteristic of epigenetic gene silencing, which may occur at the transcriptional or post-transcriptional level (Vaucheret, et al. 1998. "Transgene-induced gene silencing in plants," *Plant J* 16:651-659). To determine the basis for the reduced COMT and CCOMT activities in some of the sense transgenic lines, nuclear run-on transcription analyses were performed with transcripts completed in vitro from nuclei isolated from wild type and COMT-suppressed or CCOMT-suppressed sense lines SC4 and SCC19. Nuclei were isolated from fresh leaf tissue as described by Cox and Goldberg (Cox, K. H. and Goldberg, R. B. 1988. "Analysis of plant gene expression," *Plant Molecular Biology. A Practical Approach*. C. H. Shaw, ed, Oxford, IRL Press, pp. 1-35). Run-on transcription reaction mixtures contained 125 µl nuclei, 30 µl of 1 M $(NH_4)_2SO_4$, 12 µl of 100 mM $MgCl_2$, 3 µl of 100 µM phosphocreatine, 12 µl of creatine phosphate kinase (0.25 mg/ml), 15 µl of RNasin (Promega; Madison, Wis.), 30 µl of 5 mM CTP, GTP and ATP mixture, 48 µl of water and 25 µl of $^{32}$P-UTP (NEN, 10 µCi/µl). The reaction mixture was incubated at 30° C. for 30 minutes, then treated with RNase-free DNase (30 units, Promega) and proteinase K (500 µg, GibcoBRL) at 30° C. for 20 minutes. RNA transcripts were extracted with an equal volume of phenol-chloroform (1:1), and extracted again with an equal volume of chloroform. Unincorporated nucleotide was removed by filtration through Sephadex G-50 (Amersham). Radioactivity incorporated into the synthesized RNA was then measured by slot blot hybridization. Two hundred ng of COMT, CCOMT or β-ATPase (positive control) cDNAs were denatured and transferred to a nitrocellulose membrane by UV cross-linking, and hybridized with radiolabeled RNA probe. Hybridization and washes were carried out at 65° C. according to Church and Gilbert (Church, G. H. and Gilbert, W. 1984. "Genomic sequencing," *Proc Natl Acad Sci USA* 81:65-71). Autoradiographs were quantified using a Molecular Dynamics phosphorimager. The results indicated that the transcription rates of both COMT and CCOMT were essentially the same in wild type and down-regulated lines. However, the data from the RNA gel blot analysis mentioned above indicated that the steady state transcript levels in the sense COMT and CCOMT lines were only a fraction of the control levels, consistent with post-transcriptional gene silencing being responsible for reduced COMT and CCOMT expression in the sense transgene lines.

Table I summarizes the COMT and CCOMT activity, lignin content, and lignin composition of selected transgenic alfalfa lines harboring alfalfa COMT and CCOMT sequences in the sense or antisense orientations. Levels of acetyl bromine (AcBr) lignin and Klason lignin are expressed as % of dry matter. Levels of S, G and 5OHG are expressed as mmol/g dry weight. Down-regulation of COMT had no effect on the activity of CCOMT, and vice-versa, with one notable exception. The reduction of CCOMT to less than 4% of wild type activity in line ACC305 was associated with an approximate doubling of COMT activity as compared to wild-type levels, a finding consistent with the western blot data noted above.

Lignin content in the various lines was determined according to standard procedures for Kiason and acetyl bromide soluble lignin (Lin, S. Y. and Dence, C. W. eds, *Methods in Lignin Chemistry*, Springer Series in Wood Science, Springer-Verlag, Berlin, Heidelberg, 1992). Two hundred milligrams of dried sample was used for lignin analysis, and Klason lignin content was calculated as weight percentage of the extract-free sample.

Klason lignin levels of three independent control lines averaged 17.6% of dry matter; this value was reduced to between 15.3% and 12.5% in all lines with down-regulated COMT or CCOMT activity. The largest reductions in Klason lignin (down to 70% of the wild type value) were in lines with gene silenced COMT. However, Klason lignin was also reduced in line ACC305, which has only 3.6% of the wild type CCOMT activity but nearly double the wild type COMT activity, and in line AC315, with less than 5% wild type CCOMT activity but normal COMT activity. Thus, reductions in either COMT or CCOMT activities can independently reduce Klason lignin levels in alfalfa. In contrast to the effects on Klason lignin, down-regulation of neither OMT appeared to have a significant effect on acetyl bromide extractable lignin.

TABLE I

COMT and CCOMT Activities of Select Independent Transgenic Alfalfa Lines

|  | COMT pkat/mg | CCOMT pkat/mg | AcBr Lignin % | Klason Lignin % | S Lignin | G Lignin | 5-OH Lignin | S/G |
| --- | --- | --- | --- | --- | --- | --- | --- | --- |
| 1 | 5.98 | 22.35 | 16.07 | 17.21 | 158.8 | 305.4 | 0 | 0.52 |
| 2 | 6.55 | 23.77 | 17.79 | 17.91 | 152.8 | 325.2 | 0 | 0.47 |
| 48 | 8.19 | 21.13 | 17.52 | 17.64 | 156.2 | 279.4 | 0 | 0.56 |
| SC4 | 1.06 | 20.11 | 16.48 | 12.67 | 10.4 | 227.9 | 7.4 | 0.05 |
| SC5 | 1.24 | 22.26 | 16.35 | 12.46 | 8.6 | 246.1 | 8.8 | 0.04 |
| SC52 | 1.19 | 22.36 | 16.83 | 14.15 | 17.1 | 223.7 | 1.8 | 0.07 |
| AC310 | 0.31 | 22.17 | 16.97 | 15.30 | 0 | 248.2 | 0 | 0 |
| ACC305 | 14.39 | 0.78 | 16.36 | 14.58 | 159.1 | 150.2 | 0 | 1.05 |
| ACC315 | 8.06 | 10.7 | 15.31 | 15.50 | 164.0 | 243.6 | 0 | 0.69 |
| DS14 | 0.78 | 5.59 | 16.54 | 14.72 | 54.0 | 223.7 | 0 | 0.23 |
| DA302 | 0.81 | 1.15 | 16.78 | 15.06 | 14.0 | 303.0 | 0 | 0.05 |

A qualitative and semi-quantitative analysis of the lignin in the transgenic alfalfa lines was made using histochemical staining methods. Histochemical analysis of lignin in transverse stem sections ($5^{th}$ internode) of control (wild type), antisense COMT line AC310, and antisense CCOMT line ACC305 alfalfa was performed as follows. For Maule reagent staining, hand sections of alfalfa stems were immersed in 1% (w/v) potassium permanganate solution for 5 minutes at room temperature, then washed twice with 3% hydrochloric acid until the color turned from black or dark brown to light brown. Phloroglucinol-HCl reagent was prepared by mixing two volumes of 2% (w/v) phloroglucinol in 95% ethanol with one volume of concentrated HCl. Photographs were taken within 30 minutes of staining. Staining of transverse stem sections with phloroglucinol-HCl indicated little or no reduction in staining intensity in COMT or CCOMT antisense as compared to control lines. Reduction in phloroglucinol staining is often taken as being indicative of a reduction in lignin content, although the reagent appears most specific for coniferaldehyde end groups in lignin (Lewis, N. G. and Yamamoto, E. 1990. "Lignin: occurrence, biogenesis and biodegradation," *Annu Rev Plant Physiol Plant Mol Biol* 41:455-496). In contrast, staining with Maule reagent gave a red coloration in wild type plants which was lost in COMT down-regulated lines. Such a color shift is reported to be diagnostic for reduction of S lignin (Lewis, N. G. and Yamamoto, E. 1990. *Plant Physiol Plant Mol Biol* 41:455-496).

Analysis of lignin degradation products by gas chromatography/mass spectrometry (GC/MS) following thioacidolysis is a widely used method for analysis of lignin monomer composition (Lapierre, et al. 1985. "Thioacidolysis of lignin: Comparison with acidolysis," *J Wood Chem Technol* 5:277-292), and can be extended to analyze dimer linkage patterns. Thioacidolysis and the Raney nickel desulfurization method of Lapierre et al. (Lapierre, et al. 1995. "New insight into the molecular architecture of hardwood lignins by chemical degradative method," *Res Chem Intermed* 21:397-412) were therefore used to determine lignin composition and resistant inter-unit bonds in the selected transgenic alfalfa lines. The data from such analyses shown in FIG. 4 and Table I indicate that reduction in lignin levels in plants with down-regulated COMT activity is associated with a much greater decrease in S units than in G units, resulting in a large decrease in S/G ratio, consistent with the results of histochemical staining with Maule reagent. In fact, thioacidolysis products of S lignin were not detected at all in the COMT antisense line AC310. In contrast, there was no reduction in S lignin in lines with reduced CCOMT activity, unless there was a corresponding decrease in COMT activity, as in the double sense and antisense lines. However, levels of G lignin were most strongly reduced in transgenic line ACC305, the line with the greatest decrease in CCOMT activity. Overall, the data clearly indicate that COMT down-regulation impacts both S and G lignin, with greatest effects on S lignin, whereas CCOMT down-regulation only affects G lignin in alfalfa. Reduction of CCOMT to less than 5% of wild-type activity leads to reductions in G lignin with no apparent effect on S lignin in alfalfa. This contrasts with reported reductions in both G and S lignin in transgenic tobacco down-regulated in CCOMT expression (Zhong, et al. 1998. *Plant Cell* 10:2033-2045). CCOMT would, therefore, appear to function in the biosynthesis of G lignin in alfalfa, as has been previously proposed in tobacco (Ye, et al. 1994. *Plant Cell* 6:1427-1439; Zhong, et al. 1998. *Plant Cell* 10:2033-2045) but not in S lignin biosynthesis, contrary to the model of Li, et al. based on in vitro studies of enzyme specificity (Li, et al. 2000. *J Biol Chem* 275:6537-6545).

Analysis of gas chromatogram traces from the thioacidolysis reactions revealed new peaks in the reaction products from lignin extracted from COMT down-regulated plants, as shown in FIG. 4. These peaks were identified as originating from 5-hydroxyguaiacyl moieties that might be expected to be present if S lignin biosynthesis were being blocked primarily at the second methylation stage in COMT down-regulated plants. However, the levels of 5-hydroxyguaiacyl units were always much less than the corresponding reduction in S units, as shown in Table I.

In the intact lignin polymer, the various monomeric units are linked to each other through covalent bonding at a number of different positions. This gives rise to more than five major types of lignin dimers that can be analyzed by GCIMS after thioacidolysis and Raney nickel desulfurization, as illustrated by the five structures in Table II. 5-5 and 4-O 5 linkages only occur between G units, whereas β-β linkages only occur between S units. β-1, β-5 and β-6 linkages can occur between two G units or between a G and an S unit. Thus, the five basic linkage types can result in nine different lignin dimers. The levels of these various dimers were analyzed by GC/MS, from the series of control and COMT or CCOMT down-regulated alfalfa plants previously analyzed for lignin content and monomer composition. Table II depicts the dimer bonding patterns of lignin samples from wild type, COMT-suppressed, and CCOMT-suppressed alfalfa plants following determination of dimer composition by thioacidolysis followed by Raney nickel desulfurization. Units are mmol/g dry weight. The Kiason lignin levels and S/G ratios of the various lines are given in Table I. The chemical structures of a selection of the dimer linkages recovered from lignin after thioacidolysis and Raney nickel desulfurization are shown. The results in Table II indicate that reduction of COMT activity resulted in at most a small increase in the recovery of dimers consisting of two G units (5-5, 4-O-5, β-1 (G), β-5 (G), β-6 (G)). However, there was a total loss of recovered dimers with β-β or mixed β-1 or β-6 linkages, which all involve S units, in plants with reduced COMT activity. In contrast, reduction of CCOMT activity did not lead to a reduction in dimers containing S units. Rather, CCOMT down-regulation appeared to lead to increased recovery of β-5 (G) dimers but a reduction in β-6 (G) dimers. Lignin from line ACC305 had the highest proportion of β-β linked S units.

Taken together, the above data indicate that the reduction in S/G ratio caused by down-regulation of COMT results in a decreased proportion of linkages involving S units. This indicates that lignin linkage pattern is determined by monomer availability. However, there were also qualitative changes in lignin dimers resulting from OMT down-regulation. Thus, gas chromatograms of thioacidolysis/Raney nickel desulfurization products of lignin from five independent COMT down-regulated plants exhibited a major peak at 52.9 minutes retention time that was absent from corresponding traces from wild type or CCOMT down-regulated plants. The compound was analyzed by MS and shown to have a molecular ion with a mass/charge ratio (m/z) of 504, identical to that of the γ-p-coumarate ester of an S unit, a dimer previously identified in maize lignin (Grabber, et al. 1996. "p-Coumaroylated syringyl units in maize lignin: implications for β-ether cleavage by thioacidolysis," *Phytochemistry* 43:1189-1194). However, the retention time of the new dimer and its MS fragmentation pattern were similar but not identical to those of an authentic sample of the S unit coumarate ester. The appearance of the new dimer correlated with the loss of S-linked dimers from the lignin in COMT down-regulated plants (Table II).

TABLE II

Dimer Bonding Patterns of Lignin Samples from Wild Type, COMT-suppressed and CCOMT-suppressed Alfalfa

| Line | 5-5,G | 4-O-5,G | b-1,G | b-1,M | b-5,G | b-5,M | b-b,S | b-6,G | b-6,S | H-S,ester |
|---|---|---|---|---|---|---|---|---|---|---|
| 2 | 13 | 3.6 | 17.9 | 3.2 | 19.4 | 16.9 | 9.6 | 11 | 5 | 0 |
| 48 | 13.3 | 3.6 | 17.5 | 2.4 | 20.4 | 14 | 9.5 | 12.4 | 6.3 | 0 |
| SC4 | 16.6 | 4.1 | 21.9 | 0 | 24.6 | 19 | 0 | 14.2 | 0 | 9.4 |
| SC5 | 17.3 | 3.6 | 20.3 | 0 | 24.7 | 14 | 0 | 19.2 | 0 | 7.1 |
| AC310 | 15.5 | 3.4 | 19.1 | 0 | 23.7 | 15 | 0 | 10.6 | 0 | 12.4 |
| DA302 | 16.9 | 4 | 21.9 | 0 | 30.7 | 6.4 | 0 | 9 | 0 | 10.5 |
| DS14 | 15 | 3.3 | 20.7 | 0 | 21.5 | 18.9 | 0 | 12.8 | 0 | 7.5 |
| ACC305 | 11.2 | 2.9 | 18.6 | 5.2 | 22.2 | 19.5 | 14.8 | 10.1 | 6.6 | 0 |
| ACC315 | 14.8 | 3.6 | 23.5 | 5.7 | 30.1 | 10.3 | 4.5 | 6.2 | 3.1 | 0 |

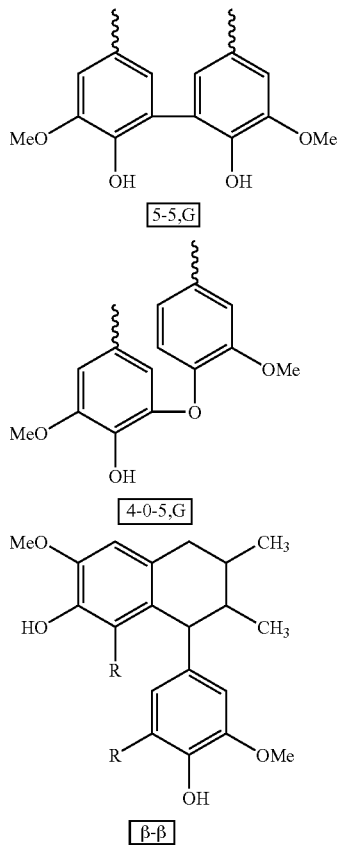

TABLE II-continued

Dimer Bonding Patterns of Lignin Samples from Wild Type, COMT-suppressed and CCOMT-suppressed Alfalfa

| Line | 5-5,G | 4-O-5,G | b-1,G | b-1,M | b-5,G | b-5,M | b-b,S | b-6,G | b-6,S | H-S,ester |
|------|-------|---------|-------|-------|-------|-------|-------|-------|-------|-----------|

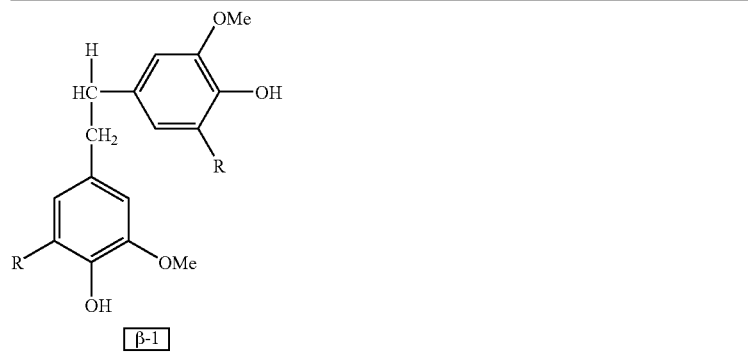

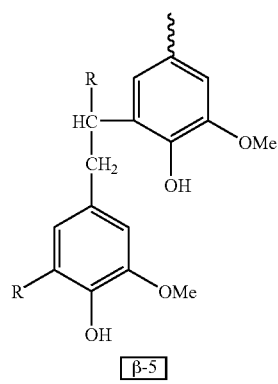

On the basis of the above analyses, line SC5 was chosen as a severely COMT down-regulated line in which recoverable S lignin was virtually absent, and line ACC305 chosen as a severely CCOMT down-regulated line in which G lignin was reduced and S/G ratio increased. Line CK48 was chosen as a control. The lines were vegetatively propagated, and greenhouse grown plants were harvested at the late bud stage, dried at 120° F., ground into 1 mm powder and put into preweighed nylon bags (approximately 5 g/bag). These bags were put into the rumens of fistulated steers for 12, 24, 36, or 72 hours of digestion. At each time point, duplicate samples for each line were analyzed in three different steers. After digestion, bags were taken out from the rumen, washed in a commercial washing machine and vacuum-dried in a freeze drier. Digestibility was calculated based on sample weight before and after digestion. The results in Table III show that total digestion of forage from all three lines reached a value of approximately 80% by 12 hours within the rumen. However, there was no further digestion of forage from the control and COMT downregulated lines beyond 24 hours in the rumen. In contrast, the forage from the CCOMT down-regulated line continued to be digested up to at least 76 hours within the rumen, attaining a value of approximately 89% digestibility.

Down-regulation of CCOMT by antisense or gene-silencing approaches was shown to be a valid method for improving forage digestibility in alfalfa, and presumably other forage legumes such as clovers and trefoils. The lack of effectiveness of strong down-regulation of COMT in significantly improving forage digestibility indicates that, contrary to current opinion, reducing S lignin is not a valid strategy for improving digestibility. Rather, it is the reduction in G lignin, which may result in a reduced level of lignin condensation, that has the major impact on digestibility of alfalfa.

TABLE III

In vivo Digestibility of Alfalfa in Fistulated Steers

| Plant Line | Time in Rumen | Digesitibility (%) | | | |
|------------|---------------|--------|--------|--------|---------|
|            |               | Steer1 | Steer2 | Steer3 | Average |
| CK48       | 12 h          | 80.00  | 78.19  | 80.83  | 79.68   |
|            | 24 h          | 83.04  | 82.95  | 83.87  | 83.29   |
|            | 36 h          | 83.98  | 83.20  | 83.91  | 83.70   |
|            | 72 h          | 84.15  | 82.34  | 82.02  | 82.83   |
| SC5        | 12 h          | 78.89  | 77.21  | 81.52  | 79.21   |
|            | 24 h          | 84.39  | 84.82  | 85.75  | 84.99   |
|            | 36 h          | 84.27  | 84.92  | 85.00  | 84.73   |
|            | 72 h          | 85.12  | 85.00  | 84.35  | 84.82   |
| ACC305     | 12 h          | 80.91  | 77.97  | 81.91  | 80.26   |
|            | 24 h          | 84.26  | 85.21  | 87.21  | 85.56   |
|            | 36 h          | 86.22  | 86.86  | 87.21  | 86.76   |
|            | 72 h          | 88.55  | 90.92  | 87.74  | 89.07   |

We claim:

1. A method for modulating lignin content of a forage legume cell comprising expressing in the cell a DNA construct comprising a promoter functionally linked to at least one open reading frame encoding for a caffeoyl CoA 3-O-methyltransferase enzyme (CCOMT) or a fragment thereof, and further expressing in said cell a DNA construct comprising at least one open reading frame encoding for a caffeic acid 3-O-methyltransferase enzyme (COMT) or a fragment thereof under expression control of a promoter, wherein expression of the at least one open reading frame encoding for the CCOMT or a fragment thereof reduces expression of the endogenous CCOMT and wherein expression of the at least one open reading frame encoding for the COMT or a fragment thereof reduces expression of the endogenous COMT in said cell.

2. The method of claim 1, wherein guaiacyl lignin content is reduced.

3. The method of claim 1 or 2, wherein the open reading frame encoding for a caffeoyl CoA 3-O-methyltransferase enzyme or a fragment thereof is in a sense orientation.

4. The method of claim 1 or 2, wherein the open reading frame encoding for a caffeoyl CoA 3-O-methyltransferase enzyme or a fragment thereof is in an antisense orientation.

5. The method of claim 3, wherein the open reading frame encoding for a caffeoyl CoA 3-O-methyltransferase enzyme or a fragment thereof is functionally linked to a bean PAL2 promoter.

6. The method of claim 4, wherein the open reading frame encoding for a caffeoyl CoA 3-O-methyltransferase enzyme or a fragment thereof is functionally linked to a bean PAL2 promoter.

7. A forage legume plant transformed with a vector comprising a DNA construct comprising a promoter functionally linked to at least one open reading frame encoding for a caffeoyl CoA 3-O-methyltransferase enzyme (CCOMT) or a fragment thereof; and comprising a DNA construct comprising at least one open reading frame encoding for a caffeic acid 3-O-methyltransferase enzyme (COMT) or a fragment thereof under expression control of a promoter, wherein expression of the at least one open reading frame encoding for the CCOMT or a fragment thereof reduces expression of the endogenous CCOMT and wherein expression of the at least one open reading frame encoding for the COMT or a fragment thereof reduces expression of the endogenous COMT in said forage legume plant.

8. The method of claim 1, wherein the open reading frame encoding for a caffeic acid 3-O-methyltransferase enzyme or a fragment thereof is in a sense orientation.

9. The method of claim 1, wherein the open reading frame encoding for a caffeic acid 3-O-methyltransferase enzyme or a fragment thereof is in an antisense orientation.

10. The method of claim 8, wherein the open reading frame encoding for a caffeic CoA 3-O-methyltransferase enzyme or a fragment thereof is functionally linked to a bean PAL2 promoter.

11. The method of claim 10, wherein the open reading frame encoding for a caffeic CoA 3-O-methyltransferase enzyme or a fragment thereof is functionally linked to a bean PAL2 promoter.

* * * * *

SEQUENCE LISTING

<160> NUMBER OF SEQ ID NOS: 4

<210> SEQ ID NO 1
<211> LENGTH: 744
<212> TYPE: DNA
<213> ORGANISM: Medicago sativa
<220> FEATURE:
<221> NAME/KEY: CDS
<222> LOCATION: (1)..(744)
<300> PUBLICATION INFORMATION:
<308> DATABASE ACCESSION NUMBER: U20736
<309> DATABASE ENTRY DATE: 1998-08-07
<313> RELEVANT RESIDUES: (36)..(779)

<400> SEQUENCE: 1

```
atg gca acc aac gaa gat caa aag caa act gaa tct gga aga cat caa      48
Met Ala Thr Asn Glu Asp Gln Lys Gln Thr Glu Ser Gly Arg His Gln
1               5                   10                  15 gaa gtt ggt cac aag agt ctt tta caa agt gat gct ctt tac cag tat      96
Glu Val Gly His Lys Ser Leu Leu Gln Ser Asp Ala Leu Tyr Gln Tyr
            20                  25                  30 att cta gag acc agt gtc ttc cca aga gaa cat gaa gcc atg aaa gag     144
Ile Leu Glu Thr Ser Val Phe Pro Arg Glu His Glu Ala Met Lys Glu
        35                  40                  45 ttg aga gag gtc aca gca aaa cac cca tgg aac atc atg aca acc tct     192
Leu Arg Glu Val Thr Ala Lys His Pro Trp Asn Ile Met Thr Thr Ser
    50                  55                  60 gca gat gaa gga caa ttt ttg agc atg ctc ctt aaa ctt atc aat gct     240
Ala Asp Glu Gly Gln Phe Leu Ser Met Leu Leu Lys Leu Ile Asn Ala
65                  70                  75                  80 aag aat acc atg gaa att ggt gtc tac act ggc tac tcc ctc ctt gcc     288
Lys Asn Thr Met Glu Ile Gly Val Tyr Thr Gly Tyr Ser Leu Leu Ala
                85                  90                  95 act gcc cta gct att cct gaa gat gga aag att ttg gct atg gac att     336
Thr Ala Leu Ala Ile Pro Glu Asp Gly Lys Ile Leu Ala Met Asp Ile
            100                 105                 110 aac aaa gaa aat tac gaa ttg ggt cta cct gta att aaa aaa gct ggt     384
Asn Lys Glu Asn Tyr Glu Leu Gly Leu Pro Val Ile Lys Lys Ala Gly
        115                 120                 125 gtt gat cac aaa att gat ttc aga gaa ggt cca gct ctt cca gtt ctt     432
Val Asp His Lys Ile Asp Phe Arg Glu Gly Pro Ala Leu Pro Val Leu
    130                 135                 140 gat gaa atg atc aaa gac gaa aag aat cat ggt agc tac gat ttc att     480
Asp Glu Met Ile Lys Asp Glu Lys Asn His Gly Ser Tyr Asp Phe Ile
145                 150                 155                 160 ttt gtg gat gct gac aaa gac aat tac ctc aac tac cat aag agg tta     528
Phe Val Asp Ala Asp Lys Asp Asn Tyr Leu Asn Tyr His Lys Arg Leu
                165                 170                 175 att gat ctt gtt aaa gtg gga ggt gtg atc ggg tac gac aac acc tta     576
Ile Asp Leu Val Lys Val Gly Gly Val Ile Gly Tyr Asp Asn Thr Leu
            180                 185                 190 tgg aat gga tct gtg gtt gca ccc cct gat gct cca ttg agg aag tat     624
Trp Asn Gly Ser Val Val Ala Pro Pro Asp Ala Pro Leu Arg Lys Tyr
        195                 200                 205 gtt agg tac tat aga gat ttt gtt ttg gag ctt aac aag gct ttg gct     672
Val Arg Tyr Tyr Arg Asp Phe Val Leu Glu Leu Asn Lys Ala Leu Ala
    210                 215                 220 gtg gac cct agg att gaa ata tgt atg ctt cct gtt ggt gat gga atc     720
Val Asp Pro Arg Ile Glu Ile Cys Met Leu Pro Val Gly Asp Gly Ile
225                 230                 235                 240
```

```
act atc tgc cgt agg atc aag taa                                  744
Thr Ile Cys Arg Arg Ile Lys
            245
```

<210> SEQ ID NO 2
<211> LENGTH: 247
<212> TYPE: PRT
<213> ORGANISM: Medicago sativa

<400> SEQUENCE: 2

```
Met Ala Thr Asn Glu Asp Gln Lys Gln Thr Glu Ser Gly Arg His Gln
1               5                   10                  15

Glu Val Gly His Lys Ser Leu Leu Gln Ser Asp Ala Leu Tyr Gln Tyr
            20                  25                  30

Ile Leu Glu Thr Ser Val Phe Pro Arg Glu His Glu Ala Met Lys Glu
        35                  40                  45

Leu Arg Glu Val Thr Ala Lys His Pro Trp Asn Ile Met Thr Thr Ser
    50                  55                  60

Ala Asp Glu Gly Gln Phe Leu Ser Met Leu Leu Lys Leu Ile Asn Ala
65                  70                  75                  80

Lys Asn Thr Met Glu Ile Gly Val Tyr Thr Gly Tyr Ser Leu Leu Ala
                85                  90                  95

Thr Ala Leu Ala Ile Pro Glu Asp Gly Lys Ile Leu Ala Met Asp Ile
            100                 105                 110

Asn Lys Glu Asn Tyr Glu Leu Gly Leu Pro Val Ile Lys Lys Ala Gly
        115                 120                 125

Val Asp His Lys Ile Asp Phe Arg Glu Gly Pro Ala Leu Pro Val Leu
    130                 135                 140

Asp Glu Met Ile Lys Asp Glu Lys Asn His Gly Ser Tyr Asp Phe Ile
145                 150                 155                 160

Phe Val Asp Ala Asp Lys Asp Asn Tyr Leu Asn Tyr His Lys Arg Leu
                165                 170                 175

Ile Asp Leu Val Lys Val Gly Gly Val Ile Gly Tyr Asp Asn Thr Leu
            180                 185                 190

Trp Asn Gly Ser Val Val Ala Pro Pro Asp Ala Pro Leu Arg Lys Tyr
        195                 200                 205

Val Arg Tyr Tyr Arg Asp Phe Val Leu Glu Leu Asn Lys Ala Leu Ala
    210                 215                 220

Val Asp Pro Arg Ile Glu Ile Cys Met Leu Pro Val Gly Asp Gly Ile
225                 230                 235                 240

Thr Ile Cys Arg Arg Ile Lys
            245
```

<210> SEQ ID NO 3
<211> LENGTH: 1098
<212> TYPE: DNA
<213> ORGANISM: Medicago sativa
<220> FEATURE:
<221> NAME/KEY: CDS
<222> LOCATION: (1)..(1098)
<300> PUBLICATION INFORMATION:
<308> DATABASE ACCESSION NUMBER: M63853
<309> DATABASE ENTRY DATE: 1997-02-10
<313> RELEVANT RESIDUES: (31)..(1128)

<400> SEQUENCE: 3

```
atg ggt tca aca ggt gaa act caa ata aca cca acc cac ata tca gat   48
Met Gly Ser Thr Gly Glu Thr Gln Ile Thr Pro Thr His Ile Ser Asp
1               5                   10                  15
```

```
gaa gaa gca aac ctc ttc gcc atg caa cta gca agt gct tca gtt ctt        96
Glu Glu Ala Asn Leu Phe Ala Met Gln Leu Ala Ser Ala Ser Val Leu
         20                  25                  30 ccc atg att ttg aaa tca gct ctt gaa ctt gat ctc tta gaa atc att       144
Pro Met Ile Leu Lys Ser Ala Leu Glu Leu Asp Leu Leu Glu Ile Ile
         35                  40                  45 gct aaa gct gga cct ggt gct caa att tca cct att gaa att gct tct       192
Ala Lys Ala Gly Pro Gly Ala Gln Ile Ser Pro Ile Glu Ile Ala Ser
 50                  55                  60 cag cta cca aca act aac cct gat gca cca gtt atg ttg gac cga atg       240
Gln Leu Pro Thr Thr Asn Pro Asp Ala Pro Val Met Leu Asp Arg Met
 65                  70                  75                  80 ttg cgt ctc ttg gct tgt tac ata atc ctc aca tgt tca gtt cgt act       288
Leu Arg Leu Leu Ala Cys Tyr Ile Ile Leu Thr Cys Ser Val Arg Thr
                 85                  90                  95 caa caa gat gga aag gtt cag aga ctt tat ggt ttg gct act gtt gct       336
Gln Gln Asp Gly Lys Val Gln Arg Leu Tyr Gly Leu Ala Thr Val Ala
                100                 105                 110 aag tat ttg gtt aag aat gaa gat ggt gta tcc att tct gct ctt aat       384
Lys Tyr Leu Val Lys Asn Glu Asp Gly Val Ser Ile Ser Ala Leu Asn
            115                 120                 125 ctc atg aat cag gat aaa gtg ctc atg gaa agc tgg tac cac cta aaa       432
Leu Met Asn Gln Asp Lys Val Leu Met Glu Ser Trp Tyr His Leu Lys
        130                 135                 140 gat gca gtc ctt gat ggg ggc att cca ttc aac aag gct tat gga atg       480
Asp Ala Val Leu Asp Gly Gly Ile Pro Phe Asn Lys Ala Tyr Gly Met
145                 150                 155                 160 aca gcc ttt gaa tac cat gga aca gat cca agg ttt aac aag gtt ttc       528
Thr Ala Phe Glu Tyr His Gly Thr Asp Pro Arg Phe Asn Lys Val Phe
                165                 170                 175 aac aag ggg atg tct gat cac tct acc atc aca atg aag aaa att ctt       576
Asn Lys Gly Met Ser Asp His Ser Thr Ile Thr Met Lys Lys Ile Leu
            180                 185                 190 gag acc tac aca ggt ttt gaa ggc ctt aaa tct ctt gtt gat gta ggt       624
Glu Thr Tyr Thr Gly Phe Glu Gly Leu Lys Ser Leu Val Asp Val Gly
        195                 200                 205 ggt ggt act gga gct gta att aac acg att gtc tca aaa tat ccc act       672
Gly Gly Thr Gly Ala Val Ile Asn Thr Ile Val Ser Lys Tyr Pro Thr
210                 215                 220 ata aag ggt ata aat ttt gat tta ccc cat gtc att gaa gat gct cca       720
Ile Lys Gly Ile Asn Phe Asp Leu Pro His Val Ile Glu Asp Ala Pro
225                 230                 235                 240 tct tat cca gga gtt gag cat gtt ggt gga gac atg ttt gtc agt att       768
Ser Tyr Pro Gly Val Glu His Val Gly Gly Asp Met Phe Val Ser Ile
                245                 250                 255 cca aag gct gat gct gtt ttt atg aag tgg att tgt cat gac tgg agt       816
Pro Lys Ala Asp Ala Val Phe Met Lys Trp Ile Cys His Asp Trp Ser
            260                 265                 270 gat gag cac tgc ttg aaa ttt ttg aag aac tgc tat gag gca ctg cca       864
Asp Glu His Cys Leu Lys Phe Leu Lys Asn Cys Tyr Glu Ala Leu Pro
        275                 280                 285 gac aat gga aaa gtg att gtg gca gaa tgc ata ctt cca gtg gct cca       912
Asp Asn Gly Lys Val Ile Val Ala Glu Cys Ile Leu Pro Val Ala Pro
290                 295                 300 gat tca agc ctg gcc aca aaa ggt gtg gtt cac att gat gtg atc atg       960
Asp Ser Ser Leu Ala Thr Lys Gly Val Val His Ile Asp Val Ile Met
305                 310                 315                 320 ttg gct cat aat cct ggt ggg aaa gag aga aca caa aaa gag ttt gag      1008
Leu Ala His Asn Pro Gly Gly Lys Glu Arg Thr Gln Lys Glu Phe Glu
                325                 330                 335
```

```
gat ctt gcc aaa ggt gct gga ttc caa ggt ttc aaa gtc cat tgt aat      1056
Asp Leu Ala Lys Gly Ala Gly Phe Gln Gly Phe Lys Val His Cys Asn
            340                 345                 350 gct ttc aac aca tac atc atg gag ttt ctt aag aag gtt taa              1098
Ala Phe Asn Thr Tyr Ile Met Glu Phe Leu Lys Lys Val
        355                 360                 365
```

<210> SEQ ID NO 4
<211> LENGTH: 365
<212> TYPE: PRT
<213> ORGANISM: Medicago sativa

<400> SEQUENCE: 4

```
Met Gly Ser Thr Gly Glu Thr Gln Ile Thr Pro Thr His Ile Ser Asp
 1               5                  10                  15

Glu Glu Ala Asn Leu Phe Ala Met Gln Leu Ala Ser Ala Ser Val Leu
                20                  25                  30

Pro Met Ile Leu Lys Ser Ala Leu Glu Leu Asp Leu Leu Glu Ile Ile
            35                  40                  45

Ala Lys Ala Gly Pro Gly Ala Gln Ile Ser Pro Ile Glu Ile Ala Ser
        50                  55                  60

Gln Leu Pro Thr Thr Asn Pro Asp Ala Pro Val Met Leu Asp Arg Met
65                  70                  75                  80

Leu Arg Leu Leu Ala Cys Tyr Ile Ile Leu Thr Cys Ser Val Arg Thr
                85                  90                  95

Gln Gln Asp Gly Lys Val Gln Arg Leu Tyr Gly Leu Ala Thr Val Ala
            100                 105                 110

Lys Tyr Leu Val Lys Asn Glu Asp Gly Val Ser Ile Ser Ala Leu Asn
        115                 120                 125

Leu Met Asn Gln Asp Lys Val Leu Met Glu Ser Trp Tyr His Leu Lys
130                 135                 140

Asp Ala Val Leu Asp Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175

Asn Lys Gly Met Ser Asp His Ser Thr Ile Thr Met Lys Lys Ile Leu
            180                 185                 190

Glu Thr Tyr Thr Gly Phe Glu Gly Leu Lys Ser Leu Val Asp Val Gly
        195                 200                 205

Gly Gly Thr Gly Ala Val Ile Asn Thr Ile Val Ser Lys Tyr Pro Thr
    210                 215                 220

Ile Lys Gly Ile Asn Phe Asp Leu Pro His Val Ile Glu Asp Ala Pro
225                 230                 235                 240

Ser Tyr Pro Gly Val Glu His Val Gly Gly Asp Met Phe Val Ser Ile
                245                 250                 255

Pro Lys Ala Asp Ala Val Phe Met Lys Trp Ile Cys His Asp Trp Ser
            260                 265                 270

Asp Glu His Cys Leu Lys Phe Leu Lys Asn Cys Tyr Glu Ala Leu Pro
        275                 280                 285

Asp Asn Gly Lys Val Ile Val Ala Glu Cys Ile Leu Pro Val Ala Pro
    290                 295                 300

Asp Ser Ser Leu Ala Thr Lys Gly Val Val His Ile Asp Val Ile Met
305                 310                 315                 320

Leu Ala His Asn Pro Gly Gly Lys Glu Arg Thr Gln Lys Glu Phe Glu
                325                 330                 335
```

```
-continued

Asp Leu Ala Lys Gly Ala Gly Phe Gln Gly Phe Lys Val His Cys Asn
            340                 345                 350

Ala Phe Asn Thr Tyr Ile Met Glu Phe Leu Lys Lys Val
            355                 360             365
```